(12) United States Patent
Chou et al.

(10) Patent No.: US 10,926,265 B2
(45) Date of Patent: Feb. 23, 2021

(54) MOLECULAR MANIPULATION AND ASSAY WITH CONTROLLED TEMPERATURE (II)

(71) Applicant: Essenlix Corporation, Monmouth Junction, NJ (US)

(72) Inventors: Stephen Y. Chou, Princeton, NJ (US); Wei Ding, Princeton, NJ (US); Yufan Zhang, Monmouth Junction, NJ (US); Hua Tan, Princeton Junction, NJ (US)

(73) Assignee: Essenlix Corporation, Monmouth Junction, NJ (US)

(*) Notice: Subject to any disclaimer, the term of this patent is extended or adjusted under 35 U.S.C. 154(b) by 0 days.

(21) Appl. No.: 16/605,853

(22) PCT Filed: Apr. 23, 2018

(86) PCT No.: PCT/US2018/028784
§ 371 (c)(1),
(2) Date: Oct. 17, 2019

(87) PCT Pub. No.: WO2018/195528
PCT Pub. Date: Oct. 25, 2018

(65) Prior Publication Data
US 2020/0376493 A1  Dec. 3, 2020

Related U.S. Application Data

(63) Continuation of application No. PCT/US2018/018108, filed on Feb. 14, 2018, and a continuation of application No. PCT/US2018/018405, filed on Feb. 15, 2018.

(60) Provisional application No. 62/488,684, filed on Apr. 21, 2017.

(51) Int. Cl.
| | | |
|---|---|---|
| *B01L 7/00* | (2006.01) | |
| *C12Q 1/60* | (2006.01) | |
| *C12Q 1/686* | (2018.01) | |

(52) U.S. Cl.
CPC .......... *B01L 7/52* (2013.01); *C12Q 1/686* (2013.01); *B01L 2200/021* (2013.01); *B01L 2200/147* (2013.01); *B01L 2300/1805* (2013.01); *B01L 2300/1861* (2013.01); *B01L 2300/1883* (2013.01)

(58) Field of Classification Search
CPC .......... B01L 7/52; B01L 2200/021; B01L 2200/147; B01L 2300/1805; B01L 2300/1861; B01L 2300/1883; C12Q 1/686
See application file for complete search history.

(56) References Cited

U.S. PATENT DOCUMENTS

| | | | |
|---|---|---|---|
| 6,376,233 B1 | 4/2002 | Wolf et al. | |
| 2002/0022219 A1 | 2/2002 | Clements et al. | |
| 2002/0094533 A1 | 7/2002 | Hess et al. | |
| 2003/0040011 A1* | 2/2003 | Barth | G01N 35/028 435/7.1 |
| 2003/0124506 A1 | 7/2003 | Bedingham et al. | |
| 2005/0181403 A1* | 8/2005 | Rava | B01L 3/5085 435/6.12 |

(Continued)

FOREIGN PATENT DOCUMENTS

WO    2017048871 A1    3/2017

*Primary Examiner* — Nicole M Ippolito

(57) ABSTRACT

The present invention provides devices, systems, and methods for rapid and easy-to-use in sample thermal cycling or temperature changes for the facilitation of reactions such as but not limited to PCR.

57 Claims, 13 Drawing Sheets

10: first plate
20: second plate
21: inner surface
22: outer surface
90: fluidic sample
102: spacing (i.e. gap) between the two plates
112: heating layer
109: first plate thickness
209: second plate thickness

(56) References Cited

U.S. PATENT DOCUMENTS

| | | |
|---|---|---|
| 2006/0094108 A1 | 5/2006 | Yoder et al. |
| 2012/0122150 A1 | 5/2012 | Boren et al. |
| 2016/0129445 A1* | 5/2016 | Corey .................. C12Q 1/6806 435/286.1 |
| 2016/0130640 A1* | 5/2016 | Wright ................ B01F 7/00141 506/39 |

* cited by examiner

A

B

- 10: first plate
- 20: second plate
- 21: inner surface
- 22: outer surface
- 90: fluidic sample
- 102: spacing (i.e. gap) between the two plates
- 112: heating layer
- 109: first plate thickness
- 209: second plate thickness

A

B

A

Q-card
Second plate
First plate
Hinge

Heating element

B

Signal sensor (Optional)

Q-card
Heating element

Heat sink (Optional)

MOLECULAR MANIPULATION AND ASSAY WITH CONTROLLED TEMPERATURE (II)

CROSS-REFERENCING

This application is a § 371 national stage application of International Application PCT/US2018/028784 filed on Apr. 23, 2018, which claims the benefit of priority to U.S. Provisional Patent Application (USPPA) No. 62/488,684, filed on Apr. 21, 2017, PCT Application No. PCT/US2018/018108, filed Feb. 14, 2018, and PCT Application No. PCT/US2018/018405, filed Feb. 15, 2018, the contents of which are relied upon and incorporated herein by reference in their entirety. The entire disclosure of any publication or patent document mentioned herein is entirely incorporated by reference.

BACKGROUND

In certain chemical, biological and/or medical assays repeated thermal cycles and/or rapid and/or precise temperature controls need to be implemented. One particular example is the polymerase chain reaction (PCR) for amplifying pre-determined nucleotides (e.g. DNA) in one or more samples. In a PCR, the samples are repeatedly heated and cooled to specific temperatures following a pre-set thermal control cycle. Another example is isothermal amplification of nucleic acids, where a sample needs to heat from a room temperature to 65 degree of Celsius. In certain scenarios, it is desirable to that the temperature of the samples can be changed rapidly and uniformly.

The present invention provides devices and methods for rapid thermal cycle changes and the devices and methods herein disclosed are suitable for the facilitation of reactions such as but not limited to PCR.

BRIEF DESCRIPTION OF THE DRAWINGS

The skilled artisan will understand that the drawings, described below, are for illustration purposes only. The drawings are not intended to limit the scope of the present teachings in any way. In some cases, the drawings are not in scale. In the figures that present experimental data points, the lines that connect the data points are for guiding a viewing of the data only and have no other means.

FIG. 11 shows the detailed elements of a heating source according to one embodiment.

FIG. 12 shows the detailed elements of a heating source according to one embodiment.

DETAILED DESCRIPTION OF EXEMPLARY EMBODIMENTS

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It should be noted that the Figures do not intend to show the elements in strict proportion. For clarity purposes, some elements are enlarged when illustrated in the Figures. The dimensions of the elements should be delineated from the descriptions herein provided and incorporated by reference.

The present invention provides the devices and methods for changing temperature of a sample quickly through making a sample into a uniform ultrathin thin over an area (or a relevant area), low thermal absorption and low thermal capacity of a sample holder, and an area heater elements.

In some embodiments, the sample holder is a QMAX card that has two thin plates to sandwich a sample, where the plates have a thickness from 1 um to 2 mm typically.

1. Working Principle

One objective of the present invention is increase and decrease the temperature of a sample rapidly.

Another objective of the present invention is to make one cycle of a sample temperature change (e.g. from 95° C. to 55° C.) in a few seconds.

To heat and cool a sample quickly, one need to reduce the energy that is needed to heat or cool a sample. The energy for heating and cooling a piece of material shares the same three major components: (i) thermal mass (i.e. a material's ability to absorb and store energy; larger the thermal mass, more energy needed to heat up), (ii) heat loss by radiation, and (iii) heat loss by thermal conduction/convection. To heat fast, one needs all three energy components to be small; but cool fast, one needs the first energy component to be small but the last two energy components to be large.

Through theoretical and experimental investigation, the present invention is based on certain designs that can balance and/or optimize the three components for rapid heating and cooling.

Figure 1:
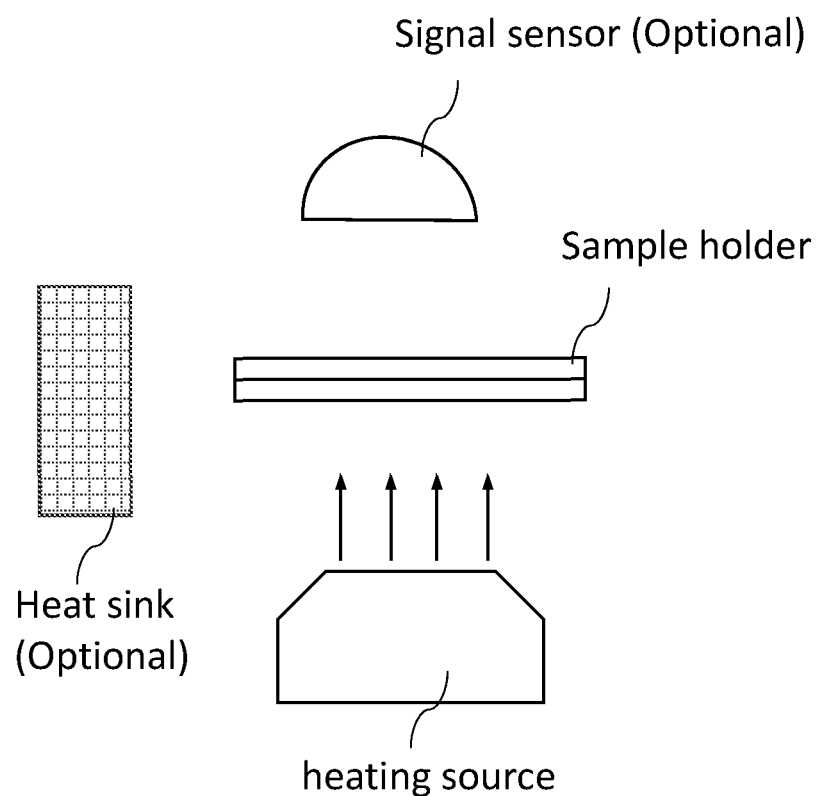
FIG. 1 shows a schematic illustration of certain components of a system for rapidly changing the temperature of a sample and for monitoring a signal from the sample.

One embodiment of the present invention, as illustrated in FIG. 1, comprises (i) a sample holder, termed "RHC (rapid heating and cooling) Card" or "sample card", that allows a rapid heating and cooling of a sample on the card; (ii) a heating system, (iii) a cooling system (optional), (iv) a temperature control system, and (v) a signal monitoring system (optional). Note that certain embodiments of the present invention can have just one or several components illustrated in FIG. 1.

The RHC card will hold a sample and reagents needed for amplifying molecules such as nucleic acids.

Clearly, the present invention can be used for different samples and for different applications.

2. Sample Card for Rapid Heating and Cooling

Figure 2:
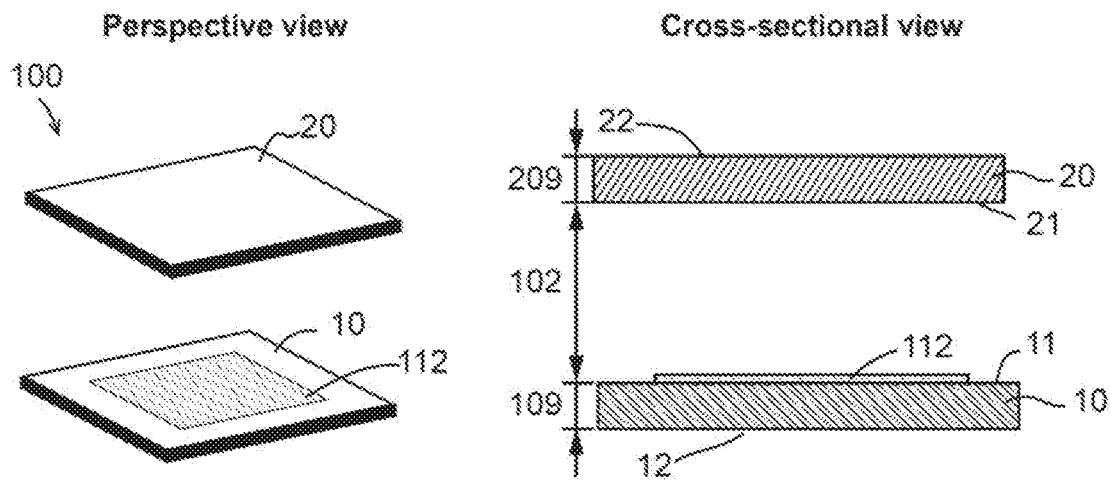
FIG. 2 shows a top view of an embodiment of a device of the present invention, demonstrating a QMAX device (or QMAX card).
Figure 2:
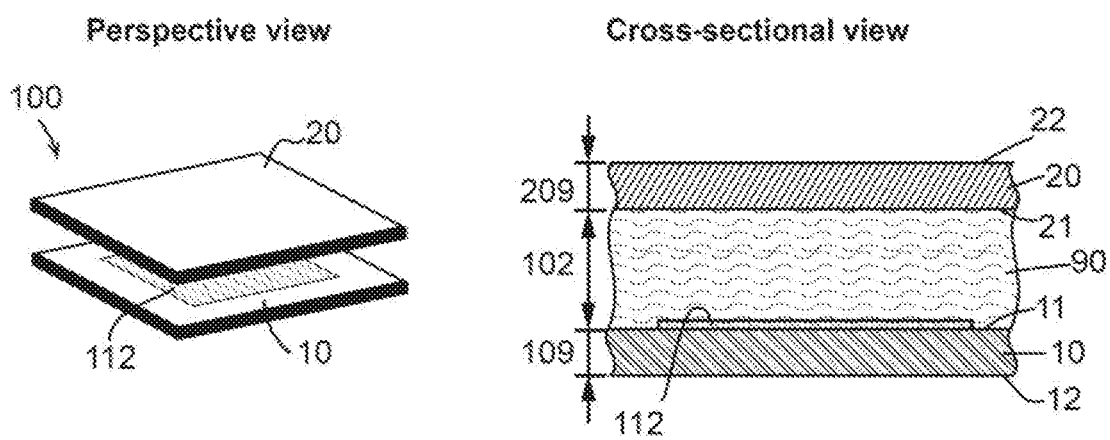

An embodiment of sample card (i.e. RHC card) is illustrated in FIG. 2. The RHC card can hold a sample and allows a rapid heating and cooling.

1. An embodiment of the RHC card for rapidly changing a fluidic sample's temperature, as illustrated in FIG. 2, comprising:
    a first plate (10), a second plate (20), and a heating layer (112), wherein:
    i. the plates (10, 20) are movable relative to each other into different configurations;
    ii. each of the plates has, on its respective inner surface, a sample contact area for contacting a fluidic sample, and
    iii. the heating layer (112) is configured to heat the fluidic sample;
    wherein the heating layer is (a) on (either the inner or outer surface) or inside one of the plates, and (b) capable of being heated by a heating source, wherein the heating source delivers heat energy to the heating layer optically, electrically, by radio frequency (RF) radiation, or a combination thereof;
    wherein at least a part of a heating area of the heating layer overlaps with the sample area,
    wherein one of the configurations is an open configuration, in which: the two plates are partially or completely separated apart and the average spacing between the plates is at least 300 um; and
    wherein another of the configurations is a closed configuration which is configured after the fluidic sample is deposited on one or both of the sample contact areas in the open configuration; and in the closed configuration: at least part of the sample is compressed by the two plates into a layer, wherein the average sample thickness is 200 um or less.

In some embodiments, the device further comprises spacers that regulate at least a portion of the sample at the closed configuration, wherein the at least portion of the sample is confined by the two plates and the spacing of the two plates is regulated by the spacers (which in turn regulate the thickness of the at least portion of the sample).

Sample Thickness

To reduce the thermal mass of the sample as well as reduce the thermal convention loss in the sample, in some embodiments, the average sample thickness at the region being heated by the heating layer is 500 □m or less, 200 □m or less, 100 □m or less, 50 □m or less, 20 □m or less, 10 □m or less, 5 □m or less, 2 □m or less, 1 □m or less, 500 nm or less, 300 nm or less, 100 nm or less, 50 nm or less, or a range between any two of the values.

One preferred average sample thickness at the region being heated by the heating layer is from 0.1 um to 0.5 um, from 0.5 um to 10 um, from 10 um to 20 um, from 20 um to 30 um, from 30 um to 50 um, from 50 um to 80 um, from 80 um to 100 um, or from 100 um to 150 um.

Plate Thickness

To reduce the thermal mass of the first and second plates as well as reduce the thermal convention loss of the plates, the first plate or the second plate has a thickness of 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, or in a range between any two of these values.

A preferred thickness of the first plate or the second plate is 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, or in a range between any two of the values.

In some preferred embodiments, the thickness of the plate that has the heating layer is thinner than the other plate that does not have a heater.

In some preferred embodiments, the first plate has a thickness of 100 nm, 200 nm, 500 nm, 1 μm (micron), 2 μm, 5 μm, 10 μm, 25 μm, 50 μm, 100 μm, 125 μm, 150 μm, 175 μm, 200 μm, 250 μm, or in a range between any two of the values; while the second plate has a thickness of 25 μm, 50 μm, 100 μm, 125 μm, 150 μm, 175 μm, 200 μm, 250 μm, 500 μm, 1 mm, 1.5 mm, 2 mm, or in a range between any two of the values, In some embodiments, the average thickness for at least one of the plates is in the range of 1 to 1000 μm, 10 to 900 μm, 20 to 800 μm, 25 to 700 μm, 25 to 800 μm, 25 to 600 μm, 25 to 500 μm, 25 to 400 μm, 25 to 300 μm, 25 to 200 μm, 30 to 200 μm, 35 to 200 μm, 40 to 200 μm, 45 to 200 μm, or 50 to 200 μm.

In some embodiments, the average thickness for at least one of the plates is in the range of 50 to 75 μm, 75 to 100 μm, 100 to 125 μm, 125 to 150 μm, 150 to 175 μm, or 175 to 200 μm.

In some embodiments, the average thickness for at least one of the plates is about 50 μm, about 75 μm, about 100 μm, about 125 μm, about 150 μm, about 175 μm, or about 200 μm.

Plate Area

In some embodiments, the first plate and/or the second plate has a lateral area of 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1000 cm$^2$ or less, 5000 cm$^2$ or less, 10,000 cm$^2$ or less, 10,000 cm$^2$ or less, or in a range between any two of these values.

In some embodiment, the first plate and/or the second plate has a width of 10 mm, 20 mm, 25 mm, 30 mm, 40 mm, 50 mm, 75 mm, or in a range between any two of these values.

In some embodiment, one preferred width of the plate is from 20 mm to 40 mm.

Edge Sealing for Reducing Sample Evaporation

In some embodiment, when the plates are in a closed configuration, it comprises a sealing that seal the edges of the two plate, and the seal is configured to reduce or eliminate evaporation of the sample during the temperature change.

The sealing can be a tape, plastic seal, oil seal, or a combination of thereof.

Example (RHC Card)-1

The first plate and the second plate are made of PMMA or PET. The first and second plate have the identical size 15 mm wide and 20 mm long and 100 um (micron). 30 um height periodic spacers array are used (initially fixed on one of the plate), making the sample thickness at a closed configuration of 30 um. The heating layer is 450 nm thick gold, has 6 mm diameter, and is on outer surface of one of the plate. A 400 nm LED was used to heat the heating layer. The sample at the closed configuration has an area of a diameter of about 12 mm and over the heating layer. We used temperature sensitive dye to monitor temperature. We found that the temperature change from 30 C to 90 C can be reached in ~2 secs, and cooled from 90 C to 30 C in ~3 sec.

3. Heating Source, and Temperature Control

The heating layer in RHC card is configured to be heated by a heating source, wherein the heating source delivers heat energy to the heating layer optically, electrically, by radio frequency (RF) radiation, or a combination thereof.

Optical Heating Source

When the heating layer is heated by a heating source optically, the heating source comprises a light source, LED (light emitting diode), lasers, lamps, or a combination of thereof; while the heating layer is a material layer that significantly absorb the radiated energy from the optical heating source. The significant absorption means that the heating layer absorbs the radiated energy from the optical heating source more significantly than the sample and the plates.

Electrical Heating Source

When the heating layer is heated by a heating source electrically, the electric heating source comprises an electrical power supply that sends an electrical power, though electrical wiring, to the heating layer.

4. Sample Signal Monitoring

Figure 11:
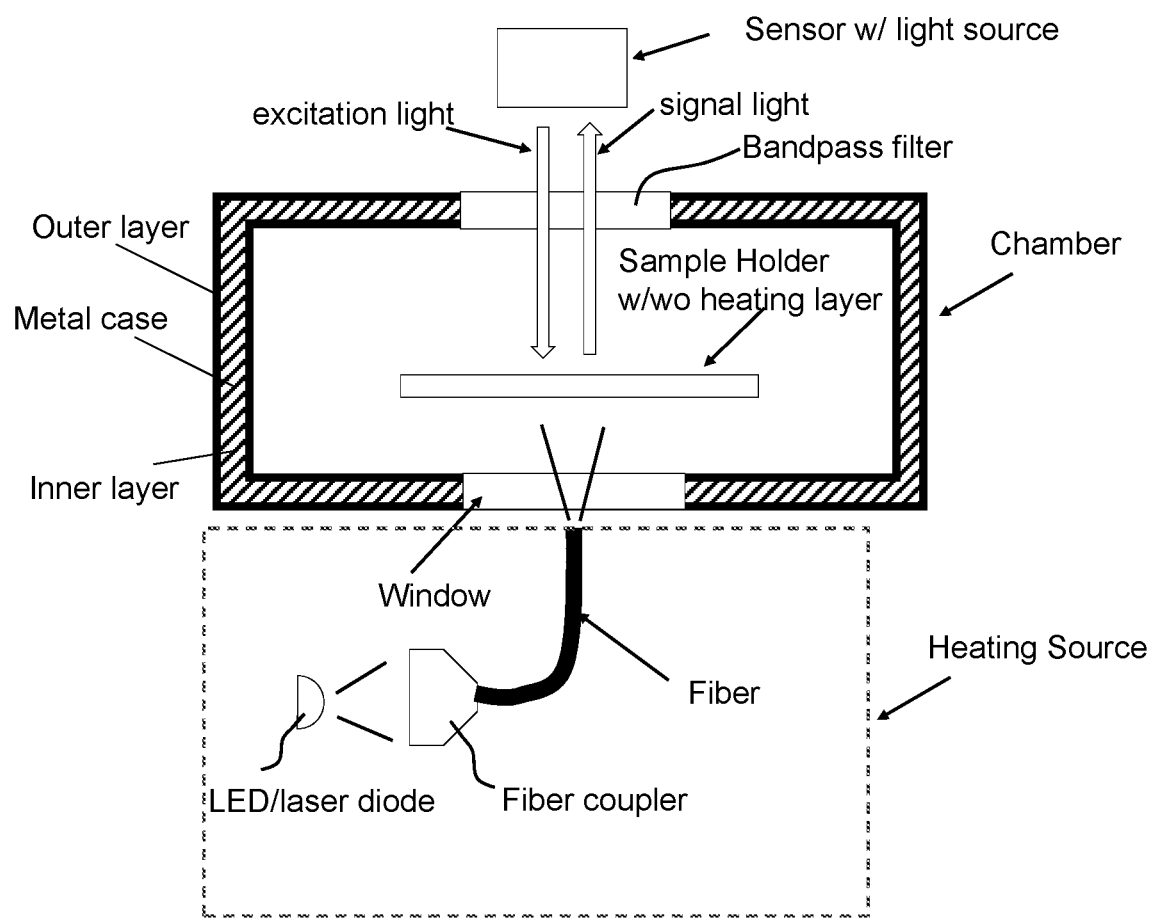
FIG. 11 shows a sectional view of an exemplary embodiment of the present invention, demonstrating the system to rapidly change the temperature of a sample.
Figure 12:
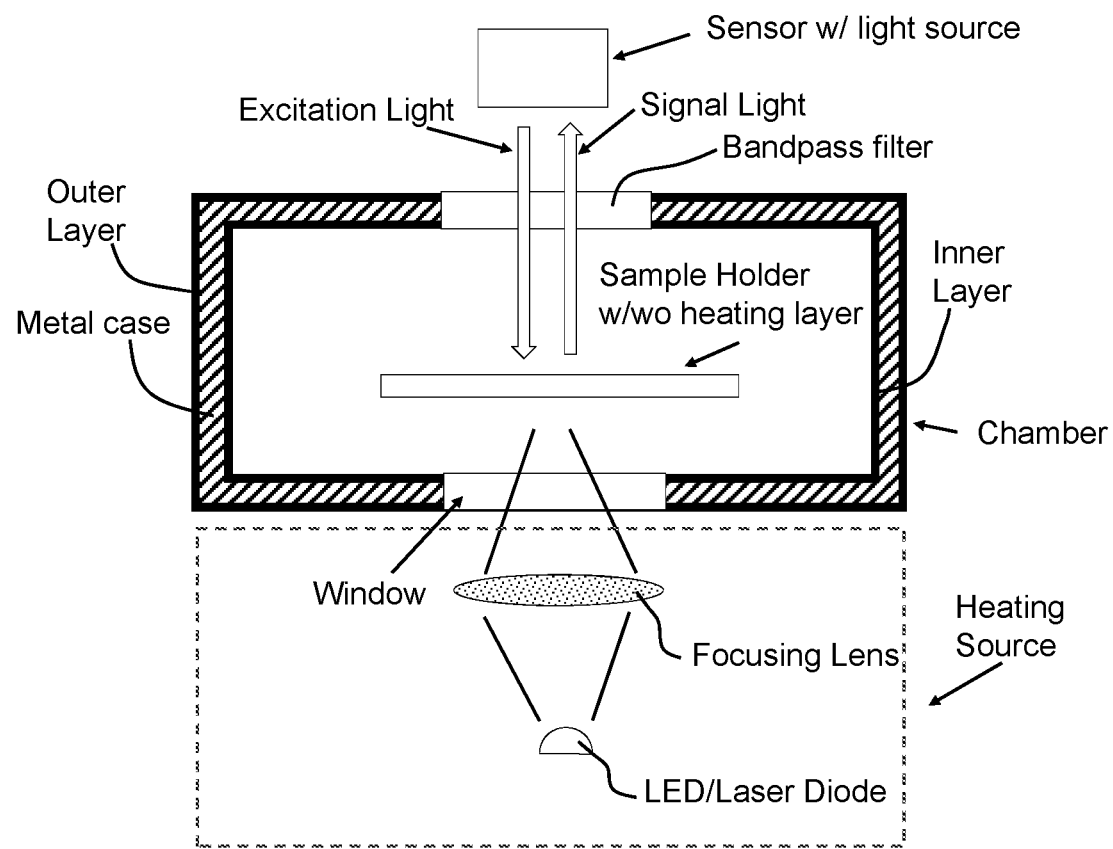
FIG. 12 shows a sectional view of an exemplary embodiment of the present invention, demonstrating the system to rapidly change the temperature of a sample.

As shown in FIGS. 11 and 12, a signal sensor can be used to detect the signal from the sample in the sample holder.

In some embodiments, the signal sensor is an optical sensor that is configured to image the fluidic sample. For example, optical sensor is a photodetector, camera, or a device capable of capturing images of the fluidic sample. In some embodiments, the optical sensor can be a camera. In some embodiments, the camera is a camera integrated into a mobile device (e.g. a smartphone or tablet computer). In some embodiments, the camera is separated from other parts of the system.

In some embodiments, the signal sensor is an electrical sensor that is configured to detect electrical signals from the device. In some embodiments, the signal sensor is a mechanical sensor that is configured to detect mechanical signals from the device.

In some embodiments, the signal sensor is configured to monitor the amount of an analyte in the sample. In some embodiments, the signal sensor is outside the chamber and receive optical signals from the sample through an optical aperture on the chamber.

5. Sample Types

The devices, systems, and methods herein disclosed can be used for samples such as but not limited to diagnostic sample, clinical sample, environmental sample and foodstuff sample. The types of sample include but are not limited to the samples listed, described and summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, systems, and methods herein disclosed are used for a sample that includes cells, tissues, bodily fluids and/or a mixture thereof. In some embodiments, the sample include fresh or processed bodily fluid, such as but not limited to: amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled condensate.

In some embodiments, the devices, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, systems, and methods are applied.

In some embodiments, the devices, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, preprocessed food as well as partially or fully processed food, etc. For example, in some embodiments the foodstuff sample includes In certain embodiments, samples that are not in liquid form are converted to liquid form before the subject devices, systems, and methods are applied.

The subject devices, systems, and methods can be used to analyze any volume of the sample. Examples of the volumes include, but are not limited to, about 10 mL or less, 5 mL or less, 3 mL or less, 1 microliter (μL, also "uL" herein) or less, 500 μL or less, 300 μL or less, 250 μL or less, 200 μL or less, 170 μL or less, 150 μL or less, 125 μL or less, 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values.

In some embodiments, the volume of the sample includes, but is not limited to, about 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values. In some embodiments, the volume of the sample includes, but is not limited to, about 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

6. Applications

The devices, systems, and methods herein disclosed can be used in various types of biological/chemical sampling, sensing, assays and applications, which include the applications listed, described and summarized in PCT Application (designating U.S.) No. PCT/US2016/045437, which was filed on Aug. 10, 2016, and is hereby incorporated by reference by its entirety.

In some embodiments, the devices, systems, and methods herein disclosed are used in a variety of different application in various field, wherein determination of the presence or absence, quantification, and/or amplification of one or more analytes in a sample are desired. For example, in certain embodiments the subject devices, systems, and methods are used in the detection of proteins, peptides, nucleic acids, synthetic compounds, inorganic compounds, and other molecules, compounds, mixtures and substances. The various fields in which the subject devices, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, systems, and methods are used in the detection of nucleic acids, proteins, or other molecules or compounds in a sample. In certain embodiments, the devices, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, systems, and methods are used to detect a fluorescence or luminescence signal. In some embodiments, the subject devices, systems, and methods include, or are used together with, a communication device, such as but not limited to: mobile phones, tablet computers and laptop computers. In some embodiments, the subject devices, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

Various samples can be used in the assays conducted with the devices, apparatus, and systems herein described. In some embodiments, the sample comprises nucleic acids. In some embodiments, the sample comprises proteins. In some embodiments, the sample carbohydrates. The current devices, apparatus, and systems can be used to rapidly change the temperature of the sample and steadily maintain the temperature of the sample, providing a fast and cost-effective approach to process samples. In addition, various applications (e.g. assays) can be conducted with the devices, apparatus, and systems herein described. Such applications include but are not limited to diagnostic testing, health monitoring, environmental testing, and/or forensic testing. Such applications also include but are not limited to various biological, chemical, and biochemical assays (e.g. DNA amplification, DNA quantification, selective DNA isolation, genetic analysis, tissue typing, oncogene identification, infectious disease testing, genetic fingerprinting, and/or paternity testing).

In some embodiments, the "sample" can be any nucleic acid containing or not containing samples, including but not limited to human bodily fluids, such as whole blood, plasma, serum, urine, saliva, and sweat, and cell cultures (mammalian, plant, bacteria, fungi). The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particles.

The term "nucleic acid" as used herein refers to any DNA or RNA molecule, or a DNA/RNA hybrid, or mixtures of DNA and/or RNA. The term "nucleic acid" therefore is intended to include but not limited to genomic or chromosomal DNA, plasmid DNA, amplified DNA, cDNA, total RNA, mRNA and small RNA. The term "nucleic acid" is also intended to include natural DNA and/or RNA molecule, or synthetic DNA and/or RNA molecule. In some embodiments, cell-free nucleic acids are presence in the sample, as used herein "cell-free" indicates nucleic acids are not contained in any cellular structures. In some other embodiments, nucleic acids are contained within cellular structures, which include but not limited to human cells, animal cells, plant cells, bacterial cells, fungi cells, and/or viral particles. Nucleic acids either in the form of cell-free nucleic acids or within cellular structures or a combination thereof, can be presence in the sample. In some further embodiments, nucleic acids are purified before introduced onto the inner surface of the first plate. In yet further embodiments, nucleic acids can be within a complex associated with other molecules, such as proteins and lipids.

The method of the invention is suitable for samples of a range of volumes. Sample having different volumes can be introduced onto the plates having different dimensions.

As used herein, "nucleic acid amplification" includes any techniques used to detect nucleic acids by amplifying (generating numerous copies of) the target molecules in samples, herein "target" refers to a sequence, or partial sequence, of nucleic acid of interest. Suitable nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

As used herein, "necessary reagents" include but not limited to, primers, deoxynucleotides (dNTPs), bivalent cations (e.g. $Mg^{2+}$), monovalent cation (e.g. $K+$), buffer solutions, enzymes, and reporters. Necessary reagents for nucleic acid amplification can be either in the dry form on the inner surface of the first or the second plate or both, or in a liquid form encased in, embedded in, or surrounded by, a material that melts with increasing temperatures, such as, for example, paraffin.

As used herein, "primers", in some embodiments, can refer to a pair of forward and reverse primers. In some embodiments, primers can refer to a plurality of primers or primer sets. As used herein, enzymes suitable for nucleic acid amplification include, but not limited to, DNA-dependent polymerase, or RNA-dependent DNA polymerase, or DNA-dependent RNA polymerase.

As used herein, the term "reporter" refers to any tag, label, or dye that can bind to, or intercalate within, the nucleic acid molecule or be activated by byproducts of the amplification process to enable visualization of the nucleic acid molecule or the amplification process. Suitable reporters include but are not limited to fluorescent labels or tags or dyes, intercalating agents, molecular beacon labels, or bioluminescent molecules, or a combination thereof.

In some other embodiments, as used herein, "necessary reagents" can also include cell lysing reagent, which facilitates to break down cellular structures. Cell lysing reagents include but not limited to salts, detergents, enzymes, and other additives. The term "salts" herein include but not limited to lithium salt (e.g. lithium chloride), sodium salt (e.g. sodium chloride), potassium (e.g. potassium chloride). The term "detergents" herein can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiotreitol (dTT), can also be included in cell lysing reagents. The compositions of necessary reagents herein vary according to rational designs of different amplification reactions.

As used herein, "nucleic acid amplification product" refers to various nucleic acids generated by nucleic acid amplification techniques. Types of nucleic acid amplification products herein include but not limited to single strand DNA, single strand RNA, double strand DNA, linear DNA, or circular DNA, etc. In some embodiments, nucleic acid amplification product can be identical nucleic acids having the same length and configuration. In some other embodiments, nucleic acid amplification products can be a plurality of nucleic acids having different lengths and configurations.

In some embodiments, nucleic acids accumulated after nucleic acid amplification is quantified using reporters. As defined and used above, reporter having quantifiable features that is correlated with the presence or the absence, or the amount of the nucleic acid amplicons accumulated in the closed chamber.

As used herein, "cell lysing reagents", intend to include but not limited to salts, detergents, enzymes, and other additives, which facilitates to disrupt cellular structures. The term "salts" herein include but not limited to lithium salt (e.g. lithium chloride), sodium salt (e.g. sodium chloride), potassium (e.g. potassium chloride). The term "detergents" herein can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiotreitol (dTT), can also be included in cell lysing reagents. The compositions of necessary reagents herein vary according to rational designs of different amplification reactions.

As used herein, "nucleic acid amplification" includes any techniques used to detect nucleic acids by amplifying (generating numerous copies of) the target molecules in samples, herein "target" refers to a sequence, or partial sequence, of nucleic acid of interest. Suitable nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification, strand displacement amplification, helicase-dependent amplification, nicking enzyme amplification, rolling circle amplification, recombinase polymerase amplification, etc.

As used herein, "necessary reagent 2" include but not limited to, primers, deoxynucleotides (dNTPs), bivalent cations (e.g. Mg2+), monovalent cation (e.g. K+), buffer solutions, enzymes, and reporters. Necessary reagent 2 for nucleic acid amplification can be either in the dry form on the inner surface of the first or the second plate or both, or in a liquid form encased in, embedded in, or surrounded by, a material that melts with increasing temperatures, such as, for example, paraffin.

As used herein, "primers", in some embodiments, can refer to a pair of forward and reverse primers. In some embodiments, primers can refer to a plurality of primers or primer sets. As used herein, enzymes suitable for nucleic acid amplification include, but not limited to, DNA-dependent polymerase, or RNA-dependent DNA polymerase, or DNA-dependent RNA polymerase.

As used herein, the term "reporter" refers to any tag, label, or dye that can bind to, or intercalate within, the nucleic acid molecule or be activated by byproducts of the amplification process to enable visualization of the nucleic acid molecule or the amplification process. Suitable reporters include but are not limited to fluorescent labels or tags or dyes, intercalating agents, molecular beacon labels, or bioluminescent molecules, or a combination thereof.

As used herein, "nucleic acid amplification product" refers to various nucleic acids generated by nucleic acid amplification techniques. Types of nucleic acid amplification products herein include but not limited to single strand DNA, single strand RNA, double strand DNA, linear DNA, or circular DNA, etc. In some embodiments, nucleic acid amplification product can be identical nucleic acids having the same length and configuration. In some other embodiments, nucleic acid amplification products can be a plurality of nucleic acids having different lengths and configurations.

In some embodiments, nucleic acids accumulated after nucleic acid amplification is quantified using reporters. As defined and used above, reporter having quantifiable features that is correlated with the presence or the absence, or the amount of the nucleic acid amplicons accumulated in the closed chamber.

Figure 13:
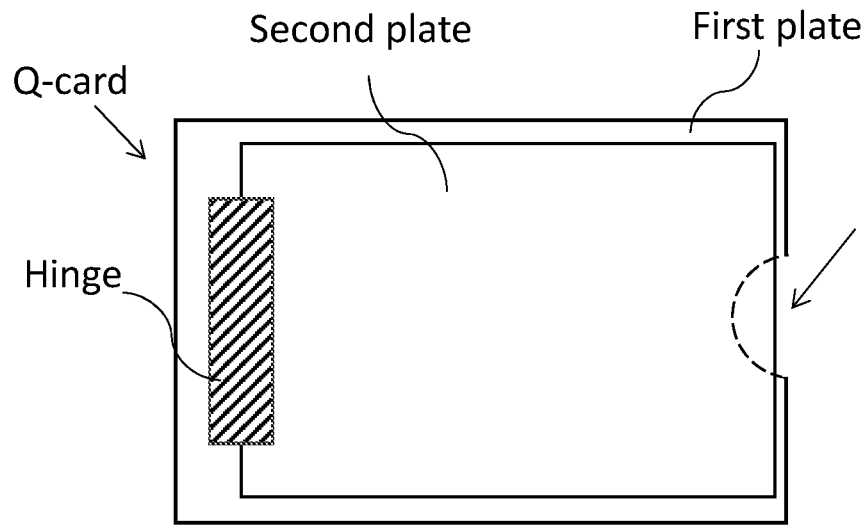
FIG. 13 shows an embodiment of the present invention, in which a heating element is not in contact with either the first plate or the second plate. Panel A illustrates a top view and panel B illustrates a side view.
Figure 13:
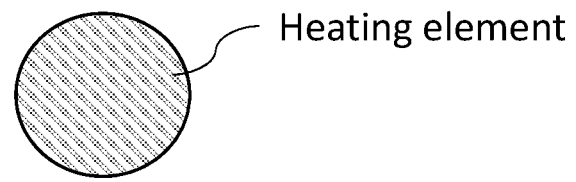
Figure 13:
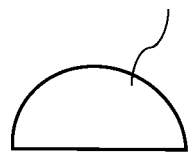
Figure 13:
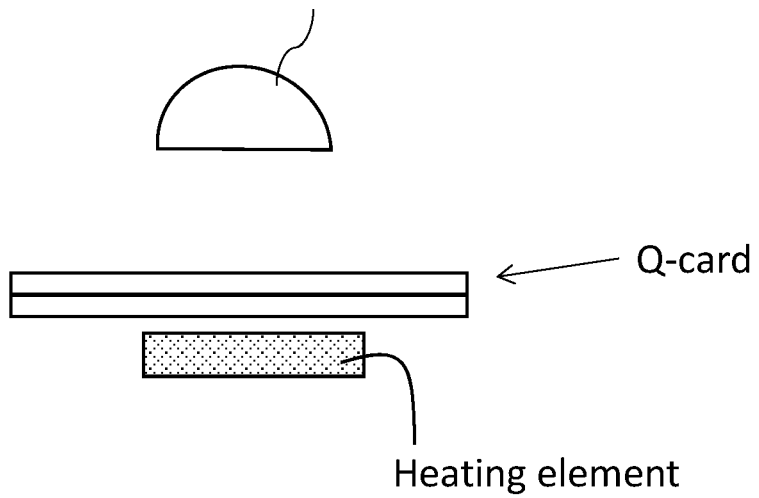
Figure 13:
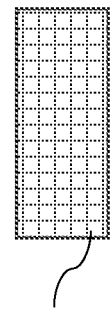

7. A Rapid Heating and Cooling Apparatus where a Separate Heating Element Outside QMAX-Card In some embodiments, the apparatus further comprise a separate heating element that is outside of RHC card and is configured to heat the RHC card when being placed near or in contact with the RHC card. The separate heating element is capable of attaching or detaching a RHC card, and gain energy from a heating source, in a similar fashion as the heating layer. The separate heating element allow a RHC card without a heating layer. For example, as shown in FIG. 13, panels A and B, the heating element is separate from the sample card.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. Nos. 62/456,065, filed on Feb. 7, 2017, which is incorporated herein in its entirety for all purposes.

A RCH card is a QMAX-care with or without spacer plus a heating layer on or inside of one of the plate.

FIG. 2 shows the QMAX card 100, which comprises a first plate 10 and a second plate 20. In some embodiments, the first plate 10 and the second plate 20 are moveable against each other into different configurations, including an open configuration and a closed configuration. In certain embodiments, in the open configuration, the two plates are partially or completely separated apart and the average spacing between the plates is at least 300 um. In certain embodiments, the sample can be deposited on one or both the plates. In certain embodiments, in the closed configuration, at least part of the sample is compressed by the two plates into a layer, wherein the average sample thickness is 200 um or less.

In some embodiments, the QMAX card 100 comprises a hinge 103 that connects the first plate 10 and the second plate 20 so that the two plates can pivot against each other. In some embodiments, the QMAX card comprises a notch 105, which facilitates the switching of the card between the open configuration and the closed configuration. In some embodiments, one or both of the plates are transparent. In some embodiments, one or both of the plates are flexible. In some embodiments, the QMAX card 100 comprises a heating layer 190. In certain embodiments, the heating layer 190 is configured to absorb electromagnetic waves and convert the energy to increase the temperature of the sample.

Figure 3:
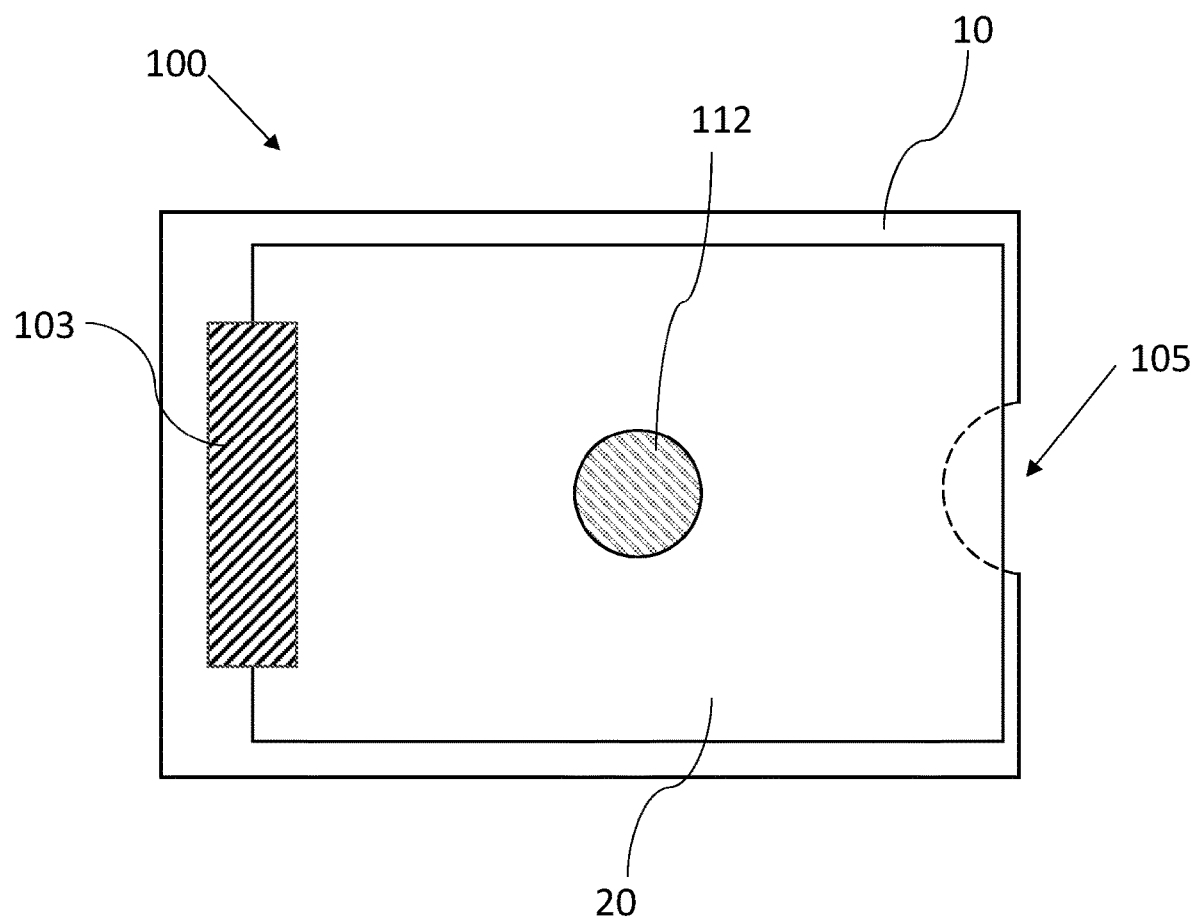
FIG. 3 shows perspective and sectional views of an embodiment of the device of the present invention; panel (A) illustrates an embodiment of the device in an open configuration; panel (B) illustrates an embodiment of the device when the sample holder is in a closed configuration, where the temperature of a sample that is compressed into a thin layer between two plates is rapidly changed by a heating source that is positioned to project electromagnetic waves onto the sample.

FIG. 3 shows perspective and sectional views of an embodiment of the device of the present invention. Panel (A) illustrates the device (also termed "sample holder" of the system) 100 in an open configuration. As shown in panel (A), the sample holder 100 comprises a first plate 10, a second plate 20, and a spacing mechanism (not shown). The first plate 10 and second plate 20 respectively comprise an outer surface (11 and 21, respectively) and an inner surface (12 and 22, respectively). Each inner surface has a sample contact area (not indicated) for contacting a fluidic sample to be processed and/or analyzed by the device.

The first plate 10 and the second plate 20 are movable relative to each other into different configurations. One of the configurations is the open configuration, in which, as shown in FIG. 3 panel (A), the first plate 10 and the second plate 20 are partially or entirely separated apart, and the spacing between the first plate 10 and the second plate 20 (i.e. the distance between the first plate inner surface 11 and the second plate inner surface 21) is not regulated by the spacing mechanism. The open configuration allows a sample to be deposited on the first plate, the second plate, or both, in the sample contact area.

As shown in panel (A) of FIG. 3, the first plate 10 further comprises a heating layer 112 in the sample contact area. It is also possible that the second plate 20 alternatively or additionally comprise the heating layer 112. In some embodiments, the heating layer 112 is configured to efficiently absorb radiation (e.g. electromagnetic waves) shed on it. The absorption percentage is 50% or more, 60% or more, 70% or more, 80% or more, 90% or more, 95% or more, 99% or more, 100% or less, 85% or less, 75% or less, 65% or less, or 55% or less, or in a range between any of the two values. The heating layer 112 is further configured to convert at least a substantial portion of the absorbed radiation energy into heat (thermal energy). For example, the heating layer 112 is configured to emit radiation in the form of heat after absorbing the energy from electromagnetic waves. The term "substantial portion" or "substantially" as used herein refers to a percentage that is 50% or more, 60% or more, 70% or more, 80% or more, 90% or more, 95% or more, 99% or more, 99% or more, or 99.9% or more.

Heating Layer Materials

In some embodiments, the heating layer 112 comprises materials/structures, such as, but not limited to, metallic plasmonic surface, metamaterials, black silicon, graphite, carbon nanotube, silicon sandwich, graphene, superlattice, plasmonic materials, any material/structure that is capable of efficiently absorbing the electromagnetic wave and converting the absorbed energy into thermal energy, and any combination thereof. In certain embodiments, the heating layer 112 comprise carbon nanotube.

In some embodiments, the heating layer comprise a dot-coupled-dots-on-pillar antenna (D2PA) array, such as, but not limited to the D2PA array described in U.S. Provisional Patent Application No. 61/347,178, which was filed on May fdir21, 2010, U.S. Provisional Patent Application 61/622,226, which was filed on Apr. 10, 2012, U.S. Provisional Patent Application No. 61/801,424, which was filed on Mar. 15, 2013, U.S. Provisional Patent Application No. 61/801,096, which was filed on Mar. 15, 2013, U.S. Provisional Patent Application No. 61/801,933, which was filed on Mar. 15, 2013, U.S. Provisional Patent Application No. 61/794,317, which was filed on Mar. 15, 2013, U.S. Provisional Patent Application No. 62/090,299, which was filed on Dec. 10, 2014, U.S. Provisional Patent Application No. 61/708,314, which was filed on Oct. 1, 2012, PCT Application No. PCT/US2011/037455, which was filed on May 20, 2011, PCT Application No. PCT/US2013/032347, which was filed on Mar. 15, 2013, PCT Application No. PCT/US2014/029979, which was filed on Mar. 15, 2014, PCT Application No. PCT/US2014/028417, which was filed on Mar. 14, 2014, PCT Application No. PCT/US2014/030108, which was filed on Mar. 16, 2014, PCT Application No. PCT/US2013/062923, which was filed on Oct. 1, 2013, U.S. patent application Ser. No. 13/699,270, which was filed on Jun. 13, 2013, U.S. patent application Ser. No. 14/459,239, which was filed on Aug. 13, 2014, U.S. patent application Ser. No. 14/871,678, which was filed on Sep. 30, 2015, U.S. patent application Ser. No. 13/838,600, which was filed on Mar. 15, 2013, U.S. patent application Ser. No. 14/459,251, which was filed on Aug. 13, 2014, U.S. patent application Ser. No. 14/668,750, which was filed on Mar. 25, 2015, U.S. patent application Ser. No. 14/775,634, which was filed on Sep. 11, 2015, U.S. patent application Ser. No. 14/775,638, which was filed on Sep. 11, 2015, U.S. patent application Ser. No. 14/852,412, which was filed on Mar. 16, 2014, U.S. patent application Ser. No. 14/964,394, which was filed on Dec. 9, 2015, U.S. patent application Ser. No. 14/431,266, which was filed on Oct. 5, 2015, the complete disclosures of which are hereby incorporated by reference for all purposes.

Panel (B) of FIG. 3 shows perspective and sectional views of the sample holder 100 when it is in a closed configuration. The sectional view illustrates part of the device without showing the entirety of the sample holder 100 or the spacing mechanism. As shown in panel (B), the sample holder 100 comprise a first plate 10, a second plate 20, and a spacing mechanism (not shown).

In FIG. 3 panel (B), the first plate 10 and the second plate 20 are in a closed configuration. In the closed configuration, the inner surfaces of the two plates 11 and 21 face each other, and the spacing between the two plates 102 is regulated by the spacing mechanism. Consequently, as shown in the figure, the two plates compress a fluidic sample 90 that is deposited on one or both of the plates into a layer, and the thickness of the layer is regulated by the spacing mechanism (not illustrated).

In some embodiments, there is aman "evaporation-prevention ring" outside of the liquid area (e.g. sample area) that prevents or reduces the vapor of the liquid escape the card, during a heating.

In some embodiments, there is clamp outside of the QMAX-card to fix the QMAX card in its closed configuration during a heating.

In some embodiments, the two plates are compressed by an imprecise pressing force, which is neither set to a precise level nor substantially uniform. In certain embodiments, the two plates are pressed directly by a human hand.

In some embodiments, the QMAX card, including the plates and spacer, is made of the material with low thermal conductivity to reduce the heat absorption by card self.

In some embodiments, there is clamp outside of the QMAX-card to fix the QMAX card in its closed configuration during a heating.

In some embodiments, the clamp is made of the material with low thermal conductivity to reduce the heat absorption by card self. In some embodiments, these materials contain but are not limit to polymers (e.g. plastics) or amorphous organic materials. The polymer materials include, not limited to, acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof. In some embodiments, these materials contain but are not limit to inorganic materials including dielectric materials of silicon oxide, porcelain, orcelain (ceramic), mica, glass, oxides of various metals, etc. In some embodiments, these materials contain but are not limit to inorganic compounds including aluminium oxide, aluminium chloride, cadmium sulfide, gallium nitride, gold chlorid, indium arsenide, lithium borohydride, silver bromide, sodium chloride, etc. In some embodiments, these materials contain liquid including but not limit to water, ethane, methane, oil, benzene, Hexane, heptane, silicone oil, polychlorinated biphenyls, liquid air, liquid oxygen, liquid nitrogen etc. In some embodiments, these materials contain gas including but not limit to air, argon, helium, nitrogen, oxygen, carbon dioxide, etc. In some embodiments, the materials is the combination of above materials.

In some embodiments of the present invention there are spacers between the two plates. In some embodiments, at least one of the spacers is in the sample contact area. In some embodiments, the spacers have uniform height. In some embodiments, the thickness of the sample is the sample as the height of the spacers.

The height of the spacers is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 μm or less, 2 μm or less, 3 μm or less, 5 μm or less, 10 μm or less, 20 μm or less, 30 μm or less, 50 μm or less, 100 μm or less, 150 μm or less, 200 μm or less, 300 μm or less, 500 μm or less, 800 μm or less, 1 mm or less, 2 mm or less, 4 mm or less, or in a range between any two of the values.

The spacer height, the spacing between the plates, and/or sample thickness is between 1 nm to 100 nm in one preferred embodiment, 100 nm to 500 nm in another preferred embodiment, 500 nm to 1000 nm in a separate preferred embodiment, 1 μm (i.e. 1000 nm) to 2 μm in another preferred embodiment, 2 μm to 3 μm in a separate preferred embodiment, 3 μm to 5 μm in another preferred embodiment, 5 μm to 10 μm in a separate preferred embodiment, and 10 μm to 50 μm in another preferred embodiment, 50 μm to 100 μm in a separate preferred embodiment.

In some embodiments, the QMAX device is fully transparent or partially transparent to reduce the heat absorption by card self wherein the transparence is above 30%, 40%, 50%, 60%, 70%, 80%, 90%, 100%, or a range between any two of the values.

In some embodiments, the QMAX device is partially reflective to reduce the heat absorption by card self. wherein the reflectance of the surface is above 30%, 40%, 50%, 60%, 70%, 80%, 90%, 100%, or a range between any two of the values.

In some embodiments, the QMAX and clamp is coated heat insulator layer to reduce the heat absorption by card self. Wherein the heat insulator layer contains materials including the low thermal conductivity material above.

In some embodiments, the clamp cover and seal all the QMAX card in close configuration.

In some embodiments, the clamp cover some of the surface of QMAX card in close configuration.

In some embodiments, the clamp has a window which is transparent to allow the light go inside the QMAX card and out from the QMAX card.

In some embodiments, the clamp is fully transparent to allow the light go inside the QMAX card and out from the QMAX card.

wherein the transparence of the clamp is above 30%, 40%, 50%, 60%, 70%, 80%, 90%, 100%, or a range between any two of the values.

In some embodiments, there is air or liquid between the clamp and QMAX device in close configuration. In certain embodiments, the liquid includes but not limit to water, ethane, methane, oil, benzene, Hexane, heptane, silicone oil, polychlorinated biphenyls, liquid air, liquid oxygen, liquid nitrogen etc. In certain embodiments, the gas includes but not limit to air, argon, helium, nitrogen, oxygen, carbon dioxide, etc.

In some embodiments, after close the clamp, the pressure on QMAX card surface applied by the clamp is 0.01 kg/cm$^2$, 0.1 kg/cm$^2$, 0.5 kg/cm$^2$, 1 kg/cm$^2$, 2 kg/cm$^2$, kg/cm$^2$, 5 kg/cm$^2$, 10 kg/cm$^2$, 20 kg/cm$^2$, 30 kg/cm$^2$, 40 kg/cm$^2$, 50 kg/cm$^2$, 60 kg/cm$^2$, 100 kg/cm$^2$, 150 kg/cm$^2$, 200 kg/cm$^2$, or a range between any two of the values; and a preferred range of 0.1 kg/cm$^2$ to 0.5 kg/cm$^2$, 0.5 kg/cm$^2$ to 1 kg/cm$^2$, 1 kg/cm$^2$ to 5 kg/cm$^2$, 5 kg/cm$^2$ to 10 kg/cm$^2$ (Pressure).

As shown in the cross-sectional views of the device in FIG. 3, the heating layer 112 spans across the sample contact area. It should be noted, however, it is also possible that the lateral area of the heating layer occupy only a portion of the sample contact area at a percentage about 1% or more, 5% or more, 10% or more, 20% or more, 50% or more, 80% or more, 90% or more, 95% or more, 99% or more, 85% or less, 75% or less, 55% or less, 40% or less, 25% or less, 8% or less, 2.5% or less. In some embodiments, in order to facilitate the temperature change of the sample, in some embodiments the lateral area of the heating layer is configured so that the sample 90 receive the thermal radiation from the heating layer 112 substantially uniformly across the lateral dimension of the sample 90 over the sample contact area.

In some embodiments, the radiation absorbing area is 10%, 30%, 40%, 50%, 60%, 70%, 80%, 90%, 100% the total plate area, or a range between any two of the values.

In some embodiments, the heating layer 112 have a thickness of 10 nm or more, 20 nm or more, 50 nm or more, 100 nm or more, 200 nm or more, 500 nm or more, 1 $\mu$m or more, 2 $\mu$m or more, 5 $\mu$m or more, 10 $\mu$m or more, 20 $\mu$m or more, 50 $\mu$m or more, 100 $\mu$m or more, 75 $\mu$m or less, 40 $\mu$m or less, 15 $\mu$m or less, 7.5 $\mu$m or less, 4 $\mu$m or less, 1.5 $\mu$m or less, 750 nm or less, 400 nm or less, 150 nm or less, 75 nm or less, 40 nm or less, or 15 nm or less, or in a range between any of the two values. In certain embodiments, the heating layer 112 have thickness of 100 nm or less.

In some embodiments, the area of the sample layer and the heating layer 112 is substantially larger than the uniform thickness. Here, the term "substantially larger" means that the general diameter or diagonal distance of the sample layer and/or the heating layer is at least 10 time, 15 times, 20 time, 25 times, 30 time, 35 times, 40 time, 45 times, 50 time, 55 times, 60 time, 65 times, 70 time, 75 times, 80 time, 85 times, 90 time, 95 times, 100 time, 150 times, 200 time, 250 times, 300 time, 350 times, 400 time, 450 times, 500 time, 550 times, 600 time, 650 times, 700 time, 750 times, 800 time, 850 times, 900 time, 950 times, 1000 time, 1500 times, 2000 times, 2500 times, 3000 time, 3500 times, 4000 time, 4500 times, or 5000 time, or in a range between any of the two values.

Figure 9:
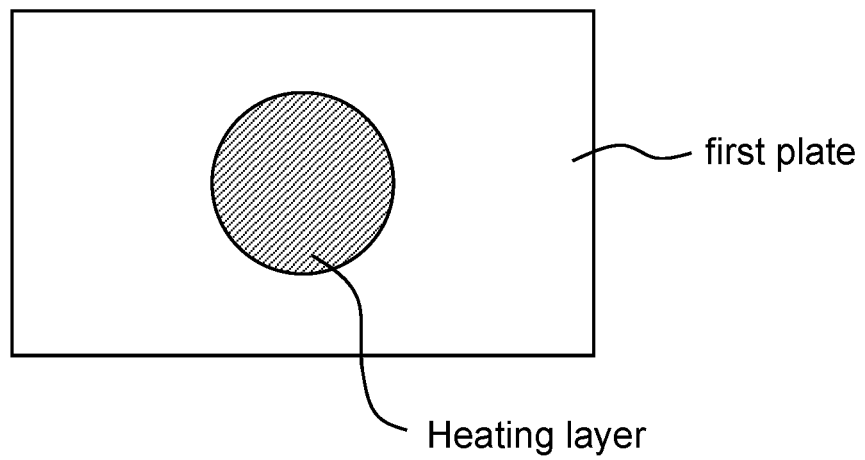
FIG. 9 shows an exemplary embodiment of the first plate and the heating layer of the present invention. Panel A is a top view and panel B is a section view.
Figure 9:
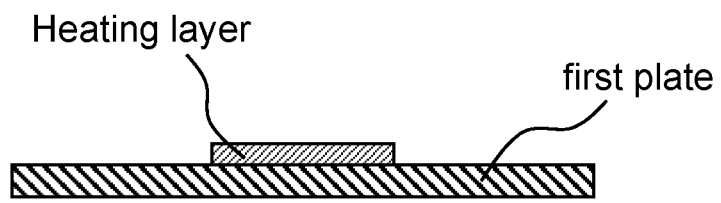
Figure 10:
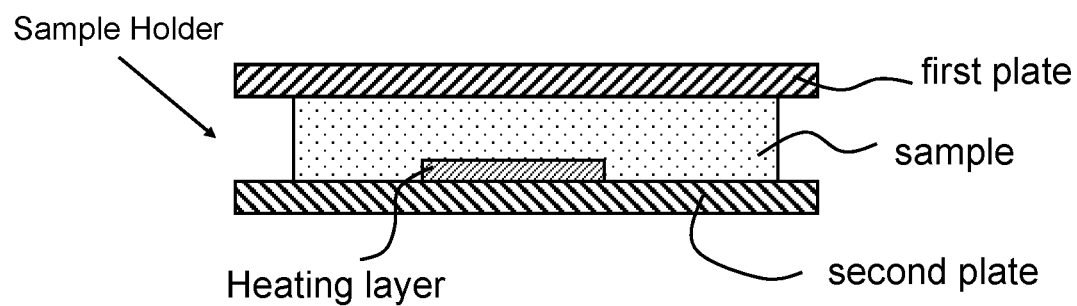
FIG. 10 shows sectional views of two exemplary embodiments of the present invention, demonstrating the first plate, the second plate, and the heating layer.
Figure 10:
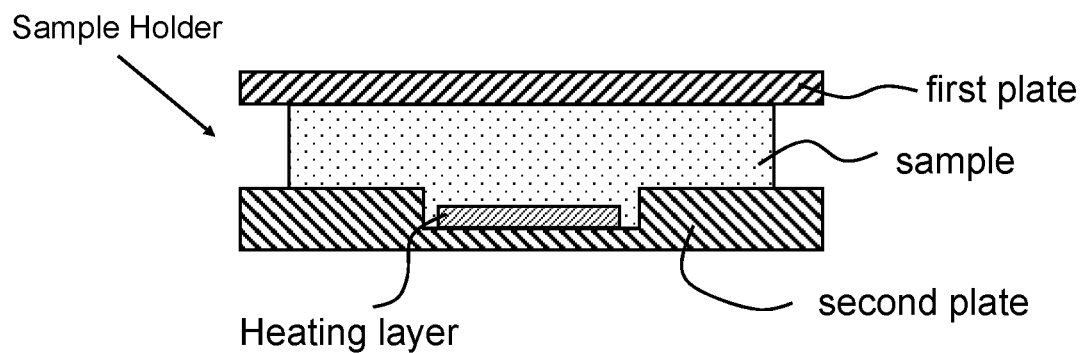

FIGS. 9 and 10 show additional embodiments of the QMAX card. FIG. 9 shows an exemplary embodiment of the first plate and the heating layer of the present invention. Panel A is a top view and panel B is a section view. FIG. 10 shows sectional views of two exemplary embodiments of the present invention, demonstrating the first plate, the second plate, and the heating layer. As a whole, the first plate and the second plate, an optically the heating layer, can be viewed as a sample holder, which refers to not only the embodiments herein shown and/or described, but also other embodiments that are capable of compressing at least part of a liquid sample into a layer of uniform thickness.

As shown in FIG. 9, panel A, in some embodiments, the heating layer is in contact with the first plate. It should be noted, however, that in some embodiments the heating layer can be in contact with the second plate 20. In addition, in some embodiments the heating layer is not in contact with any of the plates. In some embodiments, there is no separate structure of the heating layer; the first plate and/or the second plate 20 and/or the sample itself can absorb the electromagnetic radiation some that the sample's temperature can be raised.

In some embodiments, the heating layer has an area that is less than 1000 mm$^2$, 900 mm$^2$, 800 mm$^2$, 700 mm$^2$, 600 mm$^2$, 500 mm$^2$, 400 mm$^2$, 300 mm$^2$, 200 mm$^2$, 100 mm$^2$, 90 mm$^2$, 80 mm$^2$, 75 mm$^2$, 70 mm$^2$, 60 mm$^2$, 50 mm$^2$, 40 mm$^2$, 30 mm$^2$, 25 mm$^2$, 20 mm$^2$, 10 mm$^2$, 5 mm$^2$, 2 mm$^2$, 1 mm$^2$, 0.5 mm$^2$, 0.2 mm$^2$, 0.1 mm$^2$, or 0.01 mm$^2$, or in a range between any of the two values. In some embodiments, the heating layer has an area that is substantially smaller than the area of the first plate (and/or the second plate). For example, in certain embodiments, area of the heating layer occupy only a portion of the area of the first plate (or the second plate; or the sample contact area of the first plate or the second plate) at a percentage about 1% or more, 5% or more, 10% or more, 20% or more, 50% or more, 80% or more, 90% or more, 95% or more, 99% or more, 85% or less, 75% or less, 55% or less, 40% or less, 25% or less, 8% or less, 2.5% or less.

In some embodiments, the heating layer has a substantially uniform thickness. In some embodiments, the heating layer has a thickness of less than 10 nm, 20 nm, 50 nm, 100 nm, 200 nm, 500 nm, 1 $\mu$m, 2 $\mu$m, 5 $\mu$m, 10 $\mu$m, 20 $\mu$m, 50 $\mu$m, 100 $\mu$m, 200 $\mu$m, 300 $\mu$m, 400 $\mu$m, 500 $\mu$m, 600 $\mu$m, 700 $\mu$m, 800 $\mu$m, 900 $\mu$m, 1 mm, 1.5 mm, 2 mm, 2.5 mm, 3 mm, 3.5 mm, 4 mm, 4.5 mm, 5 mm, or 10 mm, or in a range between any of the two values.

The heating layer can take any shape. For example, from a top view the heating layer can be square, circle, ellipse, triangle, rectangle, parallelogram, trapezoid, pentagon, hexagon, octagon, polygon, or various other shapes.

In some embodiments, the first plate or the second plate has a thickness of 2 nm or less, 10 nm or less, 100 nm or less, 200 nm or less, 500 nm or less, 1000 nm or less, 2 $\mu$m (micron) or less, 5 $\mu$m or less, 10 $\mu$m or less, 20 $\mu$m or less, 50 $\mu$m or less, 100 $\mu$m or less, 150 $\mu$m or less, 200 $\mu$m or less, 300 $\mu$m or less, 500 $\mu$m or less, 800 $\mu$m or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values.

In some embodiments, the first plate and the second plate has a lateral area of 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1000 cm$^2$ or less, 5000 cm$^2$ or less, 10,000 cm$^2$ or less, 10,000 cm$^2$ or less, or in a range between any two of these values.

In some embodiments, the plate (either the first plate, the second plate, or both plates) that is in contact with the heating layer is thin so that the temperature of the sample can be rapidly changed. For example, in certain embodiments the plate that is in contact with the heating layer has a thickness equal to or less than 500 um, 200 um, 100 um, 50 um, 25 um, 10 um, 5 um, 2.5 um, 1 um, 500 nm, 400 nm, 300 nm, 200 nm, or 100 nm, or in a range between any of the two values. In some embodiments, if only one plate is on contact with the heating layer, the plate in contact with the heating layer is substantially thinner than the plate that is not in contact with the heating layer. For example, in some embodiments, the thickness of the plate that is in contact with the heating layer is less than $\frac{1}{1,000,000}$, $\frac{1}{500,000}$, $\frac{1}{100,000}$, $\frac{1}{50,000}$, $\frac{1}{10,000}$, $\frac{1}{5,000}$, $\frac{1}{1,000}$, $\frac{1}{500}$, $\frac{1}{100}$, $\frac{1}{50}$, $\frac{1}{10}$, $\frac{1}{5}$, or $\frac{1}{2}$ of the thickness of the plate that is in contact with the heating layer, or in a range between any of the two values.

In some embodiments, the sample layer is thin so that the temperature of the sample layer can be rapidly changed. In certain embodiments, the sample layer has a thickness equal to or less than 100 um, 50 um, 25 um, 10 um, 5 um, 2.5 um, 1 um, 500 nm, 400 nm, 300 nm, 200 nm, or 100 nm, or in a range between any of the two values.

In some embodiments, the sample holder further comprises spacers. In certain embodiments, the spacers are fixed on one or both of the plates. In certain embodiments, the spacers are mixed with the sample. In some embodiments, the spacers have a uniform height and the spacers, together with the second plate and the second plate, regulate the sample layer. In some embodiments, the thickness of the sample layer is substantially equal to the height of the spacers. In some embodiments, the plates are flat (e.g. as shown in panel A of FIG. 10). In some embodiments, either one or both of the plates include wells (e.g. as shown in panel B of FIG. 10). For example, in certain embodiments the width of the wells can be less than 500 um, 200 um, 100 um, 50 um, 25 um, 10 um, 5 um, 2.5 um, 1 um, 500 nm, 400 nm, 300 nm, 200 nm, or 100 nm, or in a range between any of the two values. In certain embodiments, the depth of the wells can be less than 500 um, 200 um, 100 um, 50 um, 25 um, 10 um, 5 um, 2.5 um, 1 um, 500 nm, 400 nm, 300 nm, 200 nm, 100 nm, 50 nm, 20 nm, 10 nm, 5 nm, 2 nm, or 1 nm, or in a range between any of the two values In various embodiments, the positioning of the heating layer can also vary. In some embodiments, as shown in FIG. 10, the heating layer is positioned at the inner surface of the first plate. Here the inner surface is defined as the surface that is in contact with the sample with the sample is compressed into a layer. The other surface is the outer surface. In some embodiments, the heating layer is at the inner surface of the first plate. In some embodiments, heating layer is at the inner surface of the second plate. In some embodiments, the heating layer is at the outer surface of the first plate. In some embodiments, the heating layer is at the outer surface the second plate. In some embodiments, there are at least two heating layers at the inner surfaces and/or outer surfaces of the first plate and/or the second plate.

As herein shown and described, in some embodiments, the sample holder is configured to compress the fluidic sample into a thin layer, thus reducing the thermal mass of the sample. But reducing the thermal mass, a small amount energy can be able to change the temperature of the sample quickly. In addition, by limiting the sample thickness, the thermal conduction is also limited.

In some embodiments, there is a sample contact area on the respective surfaces of the first plate 10 and the second plate 20. The sample contact area can be any portion of the surface of the first plate 10 and/or the second plate 20. In some embodiments, the heating layer at least partly overlaps with the sample contact area. In the overlapping part, the sample is heated quickly due to close proximity and small thermal mass.

According to some embodiments of the present invention, a sample card that can be heated and cooled rapidly is designed by using a combination and/or optimization of the following factors and designs:
  (i) The thermal masses of the card as well as the sample are minimized to reduce the energy needed for heating and the energy to be removed for cooling.
  (ii) The thermal conduction between different locations of the card and/or between different locations of the sample is reduced to allow different temperatures in the different locations. One way to achieve this is reduce the thickness of the card plates and the plate.
  (iii) The surface to volume ratio of the card plates and/or the sample is increased so that for a given volume, they have small thickness but a large area. The large area will facilitate a rapid heating and a rapid cooling (either radiative cooling and/or convection cooling.)
  (iv) A heater (e.g. a heating layer) that can rapidly heat and cool (i.e. RHC) is placed directly next and near the sample area to be heated. The separation between the sample area to the heating element of a heater is much smaller than the average diameter of the heater area (the "average diameter" is defined as the circumference of the area divided by pi (i.e. 3.14).). The heater can be an optical heater or an electrical heater of a combination, or a combination. For an optical heater, the heating elements absorb light from a light source and convert it into heat. For an electric heating, the heating element is heated by passing through an electrical current.
  (v) The radiation cooling and convention cooling are adjusted for rapid cooling.
  (vi) A heat sink for radiation cooling and/or convention cooling is used for rapid cooling.

Heating, Cooling and Control

Figure 4:
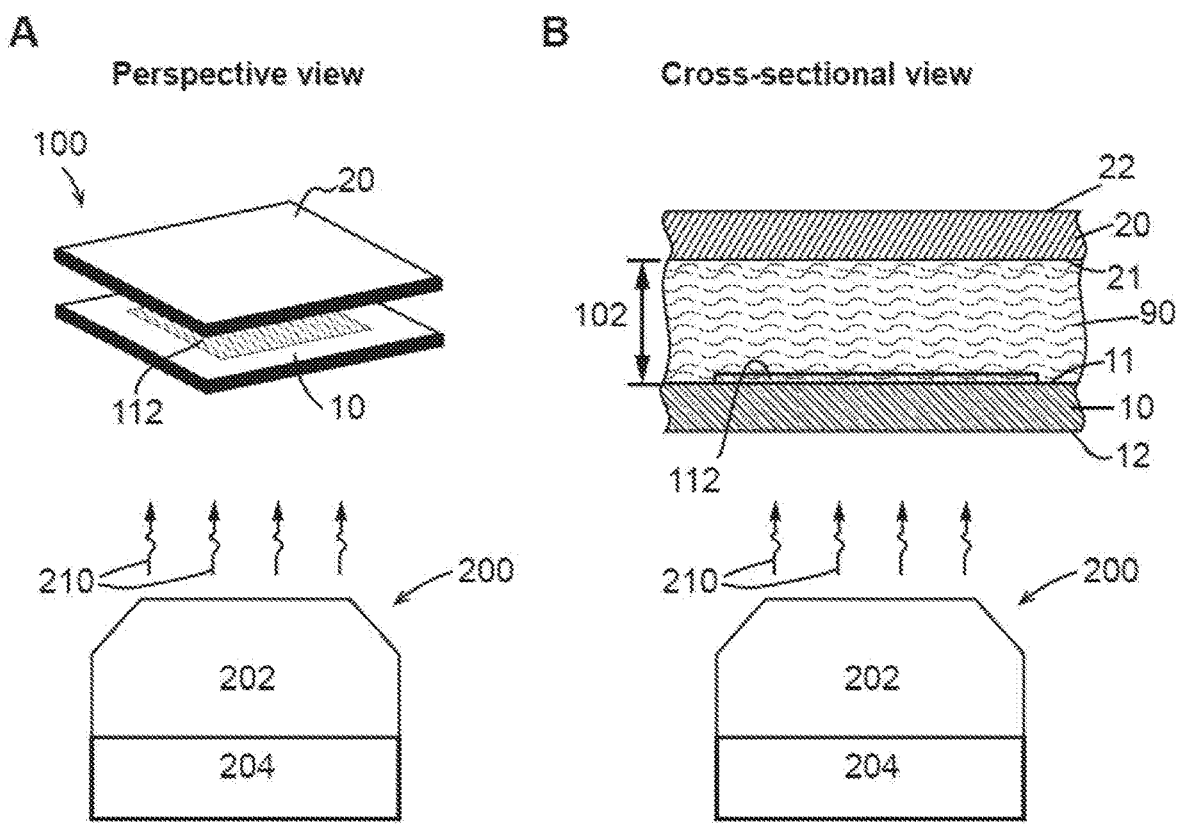
FIG. 4 shows perspective and sectional views of an embodiment of the system of the present invention; panel (A) illustrates the perspective view of the system when the device (sample holder of the system) is in an open configuration; panel (B) illustrates the sectional view of the system when the sample holder is in a closed configuration.

FIG. 4 shows perspective and sectional views of an embodiment of the system of the present invention. As shown in panels (A) and (B), in some embodiments, the system comprises a sample holder 100 and a thermal control unit 200; the sample holder 100 comprise a first plate 10, a second plate 20, and a spacing mechanism (not shown); the thermal control unit 200 comprise a heating source 202 and controller 204. Panels (A) and (B) of FIG. 2 illustrate the perspective view and sectional view of the system when the sample holder 100 of the system is in a closed configuration.

As shown in panel (B) of FIG. 3, the thermal control unit 200 comprise a heating source 202 and controller 204. In some embodiments, the thermal control unit 200 provide the energy in the form of electromagnetic waves for temperature change of the sample.

Referring to both panels (A) and (B) of FIG. 4, the heating source 202 is configured to project an electromagnetic wave 210 to the heating layer 112 of the sample holder 100, which is configured to absorb the electromagnetic wave 210 and convert a substantial portion of the electromagnetic wave 210 into heat, resulting in thermal radiation that elevate the temperature of a portion of the sample 90 that is in proximity of the heating layer 112. In other words, the coupling of the heating source 202 and the heating layer 112 is configured to generate the thermal energy that is needed to facilitate the temperature change of the sample 90.

In some embodiments, the radiation from the heating source 202 comprise radio waves, microwaves, infrared waves, visible light, ultraviolet waves, X-rays, gamma rays, or thermal radiation, or any combination thereof. In some embodiments, the heating layer 112 has a preferred range of light wavelength at which the heating layer 112 has the highest absorption efficiency. In some embodiments, the heating source 202 is configured to project the electromagnetic wave at a wavelength range within, overlapping with, or enclosing the preferred wavelength range of the heating layer 112. In other embodiments, in order to facilitate the temperature change, the wavelength is rationally designed away from the preferred wavelength of the heating layer.

In some embodiments, the heating source 202 comprise a laser source providing a laser light within a narrow wavelength range. In other embodiments, the heating source 202 comprises a LED (light-emitting diode) of a plurality thereof.

Referring to panels (A) and (B) of FIG. 4, the controller 204 is configured to control the electromagnetic wave 210 projected from the heating source 202 for the temperature change of the sample. The parameters of the electromagnetic wave 210 that the controller 204 controls include, but are not limited to, the presence, intensity, wavelength, incident angle, and any combination thereof. In some embodiments, the controller is operated manually, for instance, it is as simple as a manual switch that controls the on and off of the heating source, and therefore the presence of the electromagnetic wave projected from the heating source. In other embodiments, the controller includes hardware and software that are configured to control the electromagnetic wave automatically according to one or a plurality of pre-determined programs.

In some embodiments, the pre-determined program refers to a schedule in which the parameter(s) (e.g. presence, intensity, and/or wavelength) of the electromagnetic wave 210 is/are set to pre-determined levels for respective pre-determined periods of time. In other embodiments, the pre-determined program refers to a schedule in which the temperature of the sample 90 is set to pre-determined levels for respective pre-determined periods of time and the time periods for the change of the sample temperature from one pre-determined level to another pre-determined level are also set respectively. In some embodiments, the controller 204 is configured to be programmable, which means the controller 204 comprises hardware and software that are configured to receive and carry out pre-determined programs for the system that are delivered by the operator of the system.

Figure 5:
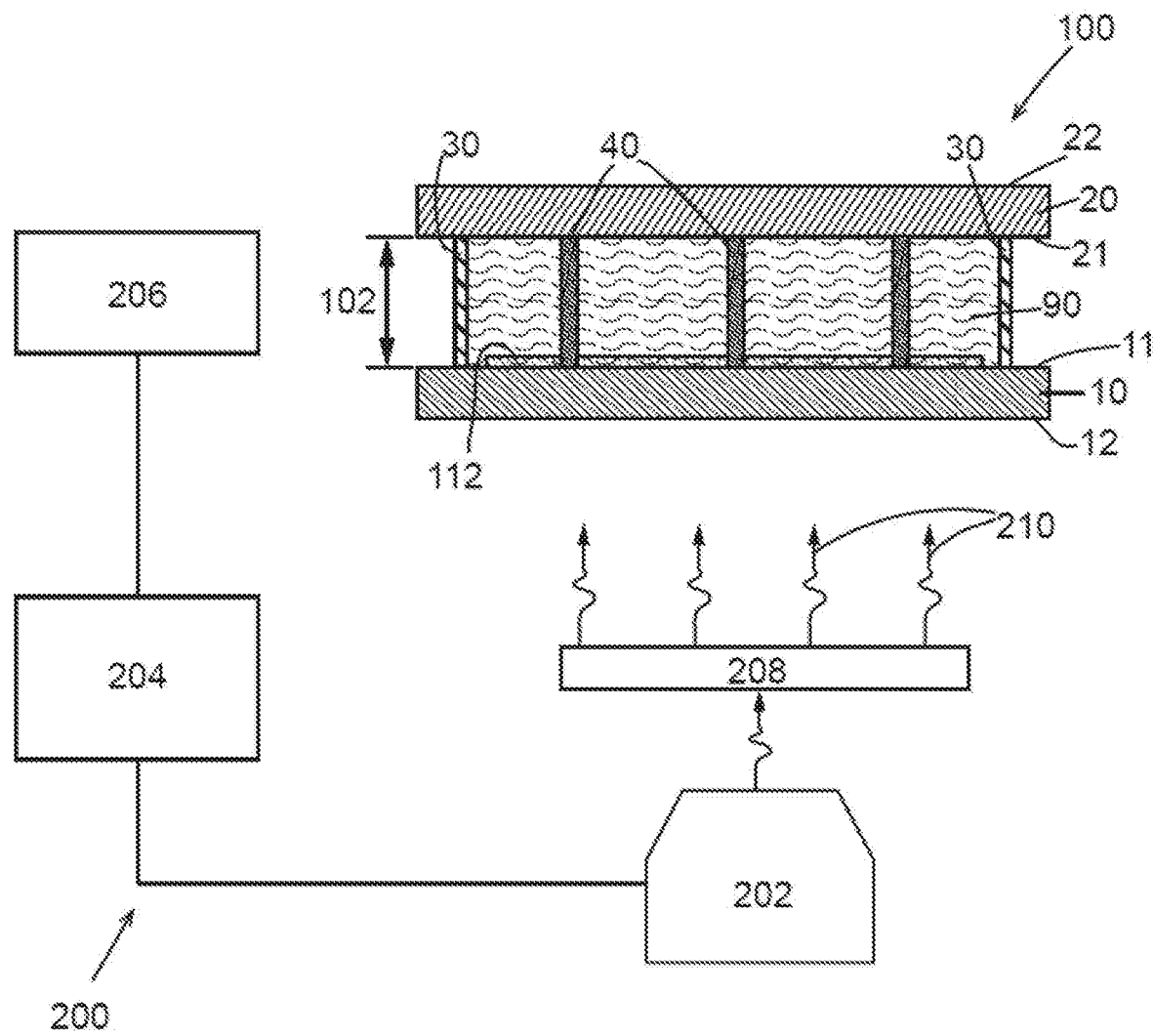
FIG. 5 shows a sectional view of an embodiment of the system of the present invention, demonstrating the system and showing additional elements that facilitate temperature change and control.

FIG. 5 shows a sectional view of an embodiment of the present invention, demonstrating the thermal cycler system and showing additional elements that facilitates temperature change and control. As shown in FIG. 5, the thermal cycler system comprises a sample holder 100 and a thermal control unit 200. The sample holder 100 comprises a first plate 10, a second plate 20, a spacing mechanism 40, and a sealing element 30; the thermal control unit 200 comprises a heating source 202, a controller 204, a thermometer 206, and an expander 208.

FIG. 5 shows the sample holder 100 in a closed configuration, in which the inner surfaces 11 and 21 of the first and second plates 10 and 20 face each other and the spacing 102 between the two plates are regulated by a spacing mechanism 40. If a sample 90 has been deposited on one or both of the plates in the open configuration, when switching to the closed configuration, the first plate 10 and the second plate 20 are pressed by a human hand or other mechanisms, the sample 90 is thus compressed by the two plates into a thin layer. In some embodiments, the thickness of the layer is uniform and the same as the spacing 102 between the two plates. In certain embodiments, the spacing 102 (and thus the thickness of the sample layer) is regulated by the spacing mechanism 40. In some embodiments, the spacing mechanism comprises an enclosed spacer that is fixed to one of the plates. In some embodiments, the spacing mechanism 40 comprises a plurality of pillar shaped spacers that are fixed to one or both of the plates. Here the term "fixed" means that the spacer(s) is attached to a plate and the attachment is maintained during at least a use of the plate.

In some embodiments, the sample holder 100 is a compressed regulated open flow (CROF, also known as QMAX) device, such as but not limited to the CROF device described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

In some embodiments, the sample holder 100 comprises a sealing element 30 that is configured to seal the spacing 102 between the first plate 10 and second plate 20 outside the medium contact area at the closed configuration. In certain embodiments, the sealing element 30 encloses the sample 90 within a certain area (e.g. the sample receiving area) so that the overall lateral area of the sample 90 is well defined and measurable. In certain embodiments, the sealing element 30 improves the uniformity of the sample 90, especially the thickness of the sample layer.

In some embodiments, the sealing element 30 comprises an adhesive applied between the first plate 10 and second plate 20 at the closed configuration. The adhesive is selective from materials such as but not limited to: starch, dextrin, gelatine, asphalt, bitumin, polyisoprenenatural rubber, resin, shellac, cellulose and its derivatives, vinyl derivatives, acrylic derivatives, reactive acrylic bases, polychloroprene, styrene-butadiene, sytyrene-diene-styrene, polyisobutylene, acrylonitrile-butadiene, polyurethane, polysulfide, silicone, aldehyde condensation resins, epoxide resins, amine base resins, polyester resins, polyolefin polymers, soluble silicates, phosphate cements, or any other adhesive material, or any combination thereof In some embodiments, the adhesive is drying adhesive, pressure-sensitive adhesive, contact adhesive, hot adhesive, or one-part or multi-part reactive adhesive, or any combination thereof. In some embodiments, the glue is natural adhesive or synthetic adhesive, or from any other origin, or any combination thereof. In some embodiments, the adhesive is spontaneous-cured, heat-cured, UV-cured, or cured by any other treatment, or any combination thereof.

In some embodiments, the sealing element 30 comprises an enclosed spacer (well). For example, the enclosed spacer has a circular shape (or any other enclosed shape) from a top view and encircle the sample 90, essentially restricting the sample 90 together with the first plate 10 and the second plate 20. In certain embodiments, the enclosed spacer (well) also function as the spacing mechanism 40. In such embodiments, the enclosed spacer seals the lateral boundary of the sample 90 as well as regulate the thickness of the sample layer.

In some embodiments, the controller 204 is configured to adjust the temperature of the sample to facilitate an assay and/or reaction involving the sample 90 according to a pre-determined program. In some embodiments, the assay and/or reaction is a PCR. In certain embodiments, the controller 204 is configured to control the presence, intensity, and/or frequency of the electromagnetic wave from the heating source 206.

As shown in FIG. 5, in some embodiments the thermal control unit 200 comprises a thermometer 206. In some embodiments, the thermometer 206 provides a monitoring and/or feedback mechanism to control/monitor/adjust the temperature of the sample 90. For example, in some embodiments the thermometer 206 is configured to measure the temperature at or in proximity of the sample contact area. In certain embodiments, the thermometer 206 is configured to directly measure the temperature of the sample 90. In some embodiments, the thermometer 206 is selected from the group consisting of: fiber optical thermometer, infrared thermometer, fluidic crystal thermometer, pyrometer, quartz thermometer, silicon bandgap temperature sensor, temperature strip, thermistor, and thermocouple. In certain embodiments, the thermometer 206 is an infrared thermometer.

In some embodiments, the thermometer 206 is configured to send signals to the controller 204. Such signals comprise information related to the temperature of the sample 90 so that the controller 204 makes corresponding changes. For example, during a PCR, for the denaturation step the target temperature is set for 95° C.; after measurement, the thermometer sends a signal to the controller 204, indicating that the measured temperature of the sample 90 is actually 94.8° C.; the controller 204 thus alters the output the heating source 202, which projects a electromagnetic wave or adjust particular parameters (e.g. intensity or frequency) of an existing electromagnetic wave so that the temperature of the sample 90 is increased to 95° C. Such measurement-signaling-adjustment loop is applied to any step in any reaction/assay.

As shown in FIG. 5, the thermal control unit 200 comprises a beam expander 208, which is configured to expand the electromagnetic wave from the heating source 202 from a smaller diameter to a larger diameter. In some embodiments, the electromagnetic wave projected from the heating source 202 is sufficient to cover the entire sample contact area; in some embodiments however, it is necessary to expand the covered area of the electromagnetic wave projected directed from the heating source 202 to produce an expanded electromagnetic wave 210, providing a heat source for all the sample contact area(s). The beam expander 208 employs any known technology, including but not limited to the bean expanders described in U.S. Pat. Nos. 4,545,677, 4,214,813, 4,127,828, and 4,016,504, and U.S. Pat. Pub. No. 2008/0297912 and 2010/0214659, which are incorporated by reference in their entireties for all purposes.

FIGS. 11 and 12 provide additional embodiments of the system. FIG. 11 shows a sectional view of an exemplary embodiment of the present invention, demonstrating the system to rapidly change the temperature of a sample. FIG. 11 shows the detailed elements of a heating source according to one embodiment.

As shown in FIG. 11 and FIG. 12, in some embodiments, the system comprises a sample holder and a heating source. In some embodiments, the sample holder comprises the first plate, the second plate, and/or the heating layer, as herein described. The heating source emits electromagnetic waves that reach the sample and can be converted to heat that raises the temperature of the sample. In some embodiments, the conversion is conducted by the heating layer. When there is no specific heating layer, the conversion is conducted by other parts of the sample holder.

As shown in FIG. 11 and FIG. 12, in some embodiments, the system comprises a chamber that encages the sample holder. In some embodiments, the chamber is an example of the heat sink in FIG. 1. In some embodiments, the chamber comprises an optical aperture that is configured to allow imaging of the sample. In some embodiments, the chamber comprises a radiation aperture configured to allow passage of electromagnetic waves from a heating source to the heating layer. In certain embodiments, a window is positioned at the radiation aperture to allow the passage of the electromagnetic waves. In certain embodiments, a filter (e.g. bandpass filter) is positioned at the optical aperture to allow the imaging of the sample in the sample holder.

In some embodiments, the chamber is used to absorb the heat from the sample and/or the heating source. In some embodiments, the chamber comprises a metal case. In some embodiments, the chamber comprises an outer layer. In certain embodiments, the outer layer is black. In some embodiments, the outer layer is made from black metal. In some embodiments, the chamber comprises an inner layer. In some embodiments, the inner layer is made from non-reflective material. In certain embodiments, the inner layer is black. In some embodiments, the inner layer is made from black metal.

As shown in FIG. 11 and FIG. 12, in some embodiments, the system comprises an optical sensor, which is configured to capture images of the fluidic sample in the sample holder. In some embodiments, the system further comprises a light source, which in some cases can be integrated with the optical sensor and in some cases can be separate. In some embodiments, the light source is configured to provide excitation light that can reach the sample. In some embodiments, the sample can provide signal light that can be captured by the optical sensor so that images are taken.

As shown in FIG. 11, in some embodiments, the heating source comprises an LED or laser diode. In certain embodiments, the heating source further comprises a fiber coupler and a fiber that direct the light from the LED/Laser diode to the sample holder.

FIG. 12 shows a sectional view of an exemplary embodiment of the present invention, demonstrating the system to rapidly change the temperature of a sample. FIG. 12 shows the detailed elements of a heating source according to one embodiment. As shown in FIG. 12, in some embodiments, the heating source comprises an LED or laser diode. In certain embodiments, the heating source further comprises one or more focusing lenses that focuses the electromagnetic waves from the heating source to the sample in the sample holder.

In some embodiments, the wavelength of the electromagnetic waves is 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 um, 10 um, 25 um, 50 um, 75 um, or 100 um, or in a range between any of the two values. In some embodiments, the wavelength of the electromagnetic waves is 100 nm to 300 nm, 400 nm to 700 nm (visible range), 700 nm to 1000 nm (IR range), 1 um to 10 um, 10 um to 100 um, or in a range between any of the two values.

Biochemistry and Assays

The thermal cycler system and associated methods of the present invention can be used to facilitate a chemical, biological or medical assay or reaction. In some embodiments, the reaction requires temperature changes. In some embodiments, the reaction requires or prefers rapid temperature change in order to avoid non-specific reaction and/or reduce wait time. In certain embodiments, the system and methods of the present invention is used to facilitate a reaction that requires cyclical temperature changes for amplification of a nucleotide in a fluidic sample; such reactions include but are not limited to polymerase chain reaction (PCR). The descriptions below use PCR as an example to illustrate the capability and utilization of the thermal cycler system and method of the present invention. It is should be noted, however, some embodiments of the device, systems and method herein described also apply to other assays and/or reactions that require temperature control and change.

In some embodiments, the assays (e.g. PCR) can be conducted with a non-processed sample. For example, the template of a PCR reaction can be provided by a sample directed obtained from a subject without additional processing. In some embodiments, the sample can be whole blood from an individual. In some embodiments, such a "one-step" approach would allow for more convenient use of the devices herein described.

In some embodiments, the sample 90 is a pre-mixed reaction medium for polymerase chain reaction (PCR). For example, in certain embodiments, the reaction medium includes components such as but not limited to: DNA template, two primers, DNA polymerase (e.g. Taq polymerase), deoxynucleoside triphosphates (dNTPs), bivalent cations (e.g. $Mg^{2+}$), monovalent cation (e.g. $K^+$), and buffer solution. The specific components, the concentrations of each component, and the overall volume varies according to rational design of the reaction.

In some embodiments, the PCR assay requires a number of changes/alterations in sample temperature between the following steps: (i) the optional initialization step, which requires heating the sample to 92-98° C.; (2) the denaturation step, which requires heating the sample to 92-98° C.; (3) the annealing step, which requires lowering the sample temperature to 50-65° C.; (4) extension (or elongation) step, which requires heating the sample to 75-80° C.; (5) repeating steps (2)-(4) for about 20-40 times; and (6) completion of the assay and lowering the temperature of the sample to ambient temperature (e.g. room temperature) or cooling to about 4° C. The specific temperature and the specific time period for each step varies and depends on a number of factors, including but not limited to length of the target sequence, length of the primers, the cation concentrations, and/or the GC percentage.

The thermal cycler system of the present invention provides rapid temperature change for the PCR assay. For example, referring to panels (A) and (B) of FIG. 3 and panel (B) of FIG. 4, in some embodiments, the sample 90 (e.g. pre-mixed reaction medium) is added to one or both of the plates 10 and 20 in the open configuration and the plates is switched to the closed configuration to compress the sample 90 into a thin layer which has a thickness 102 that is regulated by a spacing mechanism (not shown); the heating source 202 projects an electromagnetic wave 210 to the first plate 10 (e.g. specifically to the heating layer 112); the heating layer 112 is configured to absorb the electromagnetic wave 210 and convert at least a substantial portion of said electromagnetic wave 210 into heat, which increases the temperature of the sample; the removal of the electromagnetic wave 210 results in a temperature decrease in the sample 90.

In some embodiments, by projecting an electromagnetic wave 210 to the heating layer 112 or increasing the intensity of the electromagnetic wave, the thermal cycler systems provide rapid heating (increase temperature) for any or all of the initialization step, the denaturation step and/or the extension/elongation step; in some embodiments, with the removal of the electromagnetic wave projected from the heating source 202 or the decrease of the intensity of the electromagnetic wave, the cooling to the annealing step and/or the final cooling step is achieved with rapid speed. In some embodiments, the electromagnetic wave 210 or an increase of the intensity of the electromagnetic wave 210 creates an ascending temperature ramp rate of at least 50° C./s, 45° C./s, 40° C./s, 35° C./s, 30° C./s, 25° C./s, 20° C./s, 18° C./s, 16° C./s, 14° C./s, 12° C./s, 10° C./s, 9° C./s, 8° C./s, 7° C./s, 6° C./s, 5° C./s, 4° C./s, 3° C./s, or 2° C./s, or in a range between any of the two values. In certain embodiments, the average ascending temperature ramp rate in a PCR assay is 10° C./s or more. In some embodiments, the removal of the electromagnetic wave 210 or a reduction of the intensity of the electromagnetic wave 210 results in a descending temperature ramp rate of at least 50° C./s, 45° C./s, 40° C./s, 35° C./s, 30° C./s, 25° C./s, 20° C./s, 18° C./s, 16° C./s, 14° C./s, 12° C./s, 10° C./s, 9° C./s, 8° C./s, 7° C./s, 6° C./s, 5° C./s, 4° C./s, 3° C./s, or 2° C./s, or in a range between any of the two values. In certain embodiments, the average descending temperature ramp rate in a PCR assay is 5° C./s or more. As used here, the term "ramp rate" refers to the speed of temperature change between two pre-set temperatures. In some embodiments, the average ascending or descending temperature to each step is different.

During a PCR, within any step after the target temperature has been reached, the sample needs to be maintained at the target temperature for a certain period of time. The thermal cycler system of the present invention provides the temperature maintenance function by (1) adjusting the intensity of the electromagnetic wave 210, lowering it if the temperature has been raised to the target or increasing it if the temperature has been decreased to the target, and/or (2) keep the target temperature by balancing the heat provided to the sample and the heat removed from the sample.

Figure 7:
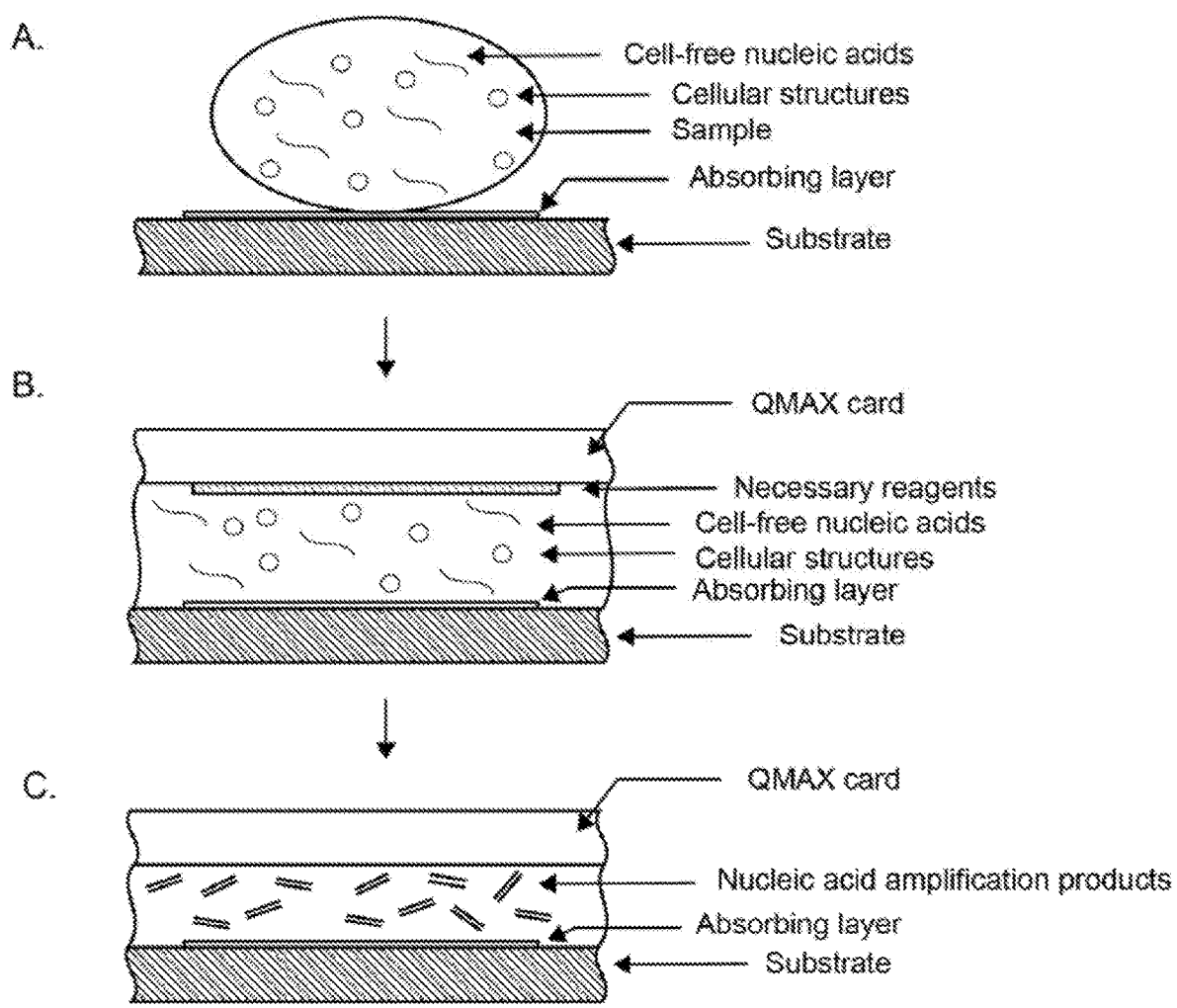
FIG. 7 shows a sectional view of an exemplary embodiment of the present invention, demonstrating how the sample is added and compressed.

FIG. 7 illustrates a cross-sectional view of an exemplary procedure for nucleic acid amplification using a QMAX card device. Examples of steps include (A) introducing sample containing nucleic acids onto the inner side of a first plate (substrate); (B) pressing a second plate (QMAX card) onto the inner surface of the first plate to form a closed configuration of the device, where necessary reagents for nucleic acid amplification are dried on the inner surface of the second plate; (c) accumulating nucleic acid amplification products in the chamber enclosed by the first and the second plates.

FIG. 7 illustrates a cross-sectional view of an exemplary procedure for nucleic acid amplification using a QMAX card device.

The sample can be introduced onto either the first plate or the second plate, or even both when necessary. FIG. 7. herein provides an example of introducing sample onto the first plate inner surface.

More particularly, in step (b), a second plate is pressed onto the inner surface of the first plate, in contact with the sample, to form a closed configuration of the device. As used herein, "a second plate" refers to a QMAX card with periodic spacers on the inner surface contacting samples.

More particularly, in step (c), when the device is in the closed configuration, a heating source projects an electromagnetic wave to the heating layer on the inner or outer surface of the first plate, or the second plate or both. The heating layer is configured to absorb the electromagnetic wave and convert at least a substantial portion of the energy from the said electromagnetic wave into the form of heat, which transmitted to the sample in the closed chamber. In some embodiments, the heating source is programmed to adjust the temperature of the said sample in a range from ambient temperature to 98° C. In some embodiments, for example for conventional PCR, the sample is first heated to 98° C., and then undergoes a repeated cycle of 94° C., 50-65° C., and 72° C. for 15-40 times. In some embodiments, for example for isothermal amplification, the temperature of the sample is maintained at a constant temperature. In some embodiments, for example when conducting isothermal amplification via LAMP, the sample is heated to 60-65° C. for about 1-70 min.

Figure 8:
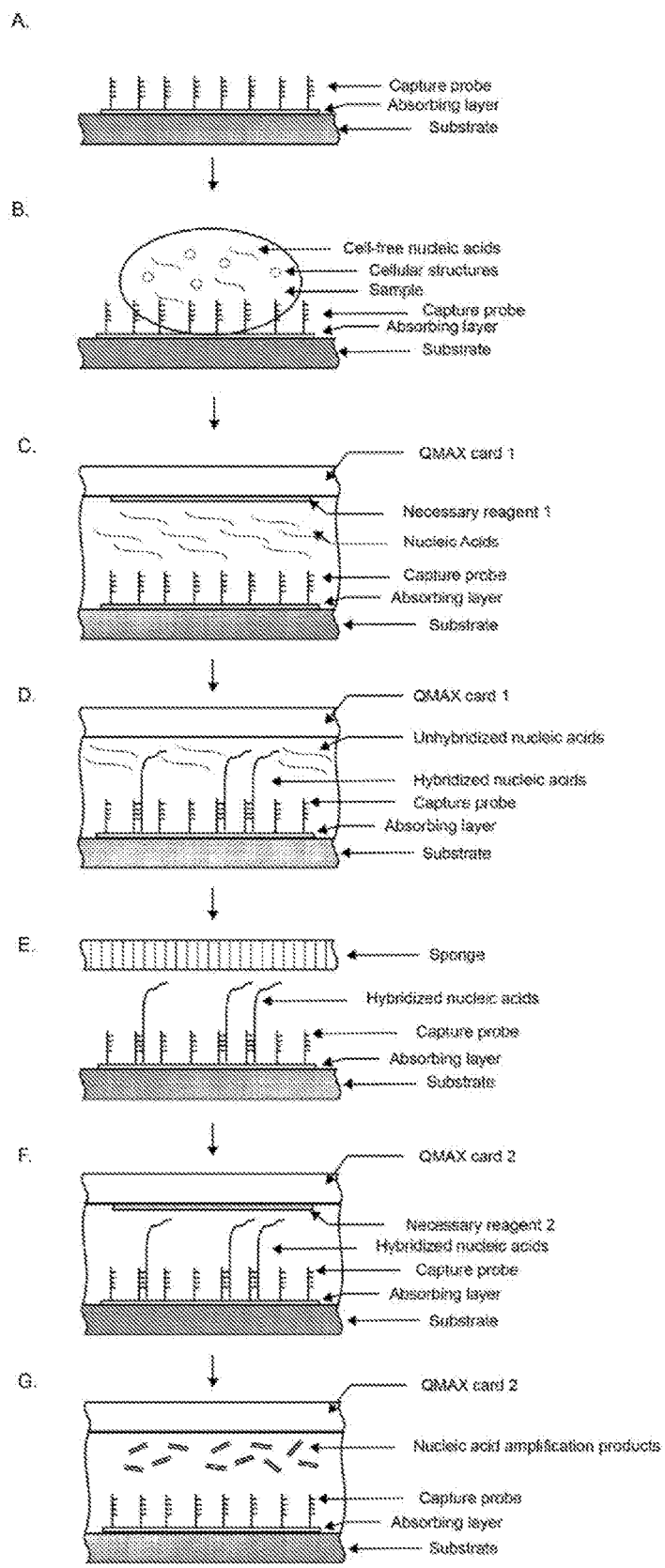
FIG. 8 shows a sectional view of an exemplary embodiment of the present invention, demonstrating a PCR process.

FIG. 8 illustrates a cross-sectional view of an exemplary assay procedure combining nucleic acid extraction and amplification using a QMAX card device. Examples of steps include (a) immobilizing capture probes on the inner surface of a first plate (substrate); (b) introducing samples onto the inner surface of the first plate; (c) pressing a second plate (QMAX card 1) onto the inner surface of the first plate to form a closed configuration of the device, where necessary reagents 1 to facilitate releasing and capturing nucleic acids are dried on the inner surface of the second plate; (d)

capturing nucleic acids from the above said sample onto the inner surface of the first plate; (e) detaching the second plate and cleaning the inner surface of the first plate using sponge; (f) pressing a third plate (QMAX card 2) onto the inner surface of the first plate, where necessary reagents 2 for nucleic acid amplification are dried on the inner surface of the third plate; (g) accumulating nucleic acid amplification products in the chamber enclosed by the first and the third plate.

More particular, in step (a), capture probes are immobilized on the inner surface of the first plate. As used herein, "capture probes" refer to oligonucleotides having the length between 1-200 bp, preferably between 5-50 bp, more preferably between 10-20 bp. Capture probes have complementary sequence to nucleic acid sequences of interest in the sample. In some embodiments, identical capture probes are immobilized on the surface of the first plate. In some other embodiments, different capture probes having different base pair compositions are immobilized on the surface of the first plate. Capture probes can be DNA, or RNA, or both, but preferably to be single strand DNA. As used herein, "immobilize" refers to a process to anchor the capture probe on the plate surface. In some embodiments, capture probes are anchored through covalent bond, wherein, for example, either 5' or 3' end of the capture probe is modified to facilitate coating on the plate surface. Commonly used 3' end modifications include but not limited to thiol, dithiol, amine, biotin, etc. In some other embodiments, capture probes can be passively absorbed on the substrate surface.

After immobilized with capture probes, the plate surface is blocked with blocker solutions. Suitable blockers include but not limited to 6-Mercapto-hexanol, bovine serum albumin, etc.

As shown in step (b) in FIG. 8, the "sample" can be any nucleic acid containing or not containing samples, including but not limited to human bodily fluids, such as whole blood, plasma, serum, urine, saliva, and sweat, and cell cultures (mammalian, plant, bacteria, fungi). The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particles.

The sample can be introduced onto either the first plate or the second plate, or even both when necessary. FIG. 8 herein provides an example of introducing sample onto the first plate inner surface.

More particularly, in step (c), a second plate (QMAX card 1) is pressed onto the inner surface of the first plate (substrate), in contact with the sample, to form a closed configuration of the device. Necessary reagents 1 for nucleic acid amplification can be either in the dry form on the inner surface of the first or the second plate or both, or in a liquid form encased in, embedded in, or surrounded by, a material that melts with increasing temperatures, such as, for example, paraffin. More particularly, in step (d), after in contact with the above said sample, dried necessary reagent 1 dissolves in the sample. Nucleic acids of interest, either released from disrupted cellular structures or presence as cell-free nucleic acids, or a combination thereof, hybridize to the complementary capture probes on the plate surface. Time used for hybridization varies, largely depending on the specifications of the spacers on the inner surface of the QMAX card 1. In some embodiments, for example, when a QMAX card 1 having 30 um spacers in height is used, experimental data indicated after 2 min, hybridization between nucleic acids of interest and immobilized capture probes reached equilibrium. As used herein FIG. 8 (*d*), "unhybridized nucleic acids" refer to nucleic acids that are not captured by the immobilized capture probes.

More particularly, in step (e) of FIG. 8, the second plate (QMAX card 1) is detached from the first plate (substrate) and the surface of the first plate (substrate) is cleaned using sponge. As used herein, "sponge" refers to a class of flexible porous materials that change pore sizes under different pressures. Sponges containing washing buffer are in contact with the first plate surface to remove contaminates. In some embodiments, sponges are in contact with the first plate surface for one time. In some other embodiments, sponges are in contact with the first plate surface for twice, or more than twice. As used herein, "contaminates" refer to compounds including but not limited to cell debris, proteins, non-specific nucleic acid, etc. that are detrimental to the nucleic acid amplification reaction.

More particularly, in step (f) of FIG. 8, a third plate (QMAX card 2) is pressed onto the inner surface of the first plate, in contact with the sample, to form a closed configuration of the device. Necessary reagent 2 for nucleic acid amplification can be either in the dry form on the inner surface of the first or the third plate or both, or in a liquid form encased in, embedded in, or surrounded by, a material that melts with increasing temperatures, such as, for example, paraffin.

More particularly, in step (g) of FIG. 8, when the device is in the closed configuration, a heating source projects an electromagnetic wave to the heating layer on the inner or outer surface of the first plate, or the third plate or both. The heating layer is configured to absorb the electromagnetic wave and convert at least a substantial portion of the energy from the said electromagnetic wave into the form of heat, which transmitted to the sample in the closed chamber. In some embodiments, the heating source is programmed to adjust the temperature of the said sample in a range from ambient temperature to 98° C. In some embodiments, for example for conventional PCR, the sample is first heated to 98° C., and then undergoes a repeated cycle of 94° C., 50-65° C., and 72° C. for 15-40 times. In some embodiments, for example for isothermal amplification, the temperature of the sample is maintained at a constant temperature. In some embodiments, for example when conducting isothermal amplification via LAMP, the sample is heated to 60-65° C. for about 1-70 min.

In some embodiments of QMAX, the sample contact area of one or both of the plates comprises a compressed open flow monitoring surface structures (MSS) that are configured to monitoring how much flow has occurred after COF. For examples, the MSS comprises, in some embodiments, shallow square array, which will cause friction to the components (e.g. blood cells in a blood) in a sample. By checking the distributions of some components of a sample, one can obtain information related to a flow, under a COF, of the sample and its components.

The depth of the MSS can be $1/1000$, $1/100$, $1/100$, $1/5$, $1/2$ of the spacer height or in a range of any two values, and in either protrusion or well form.

Multiplexing

Figure 6:
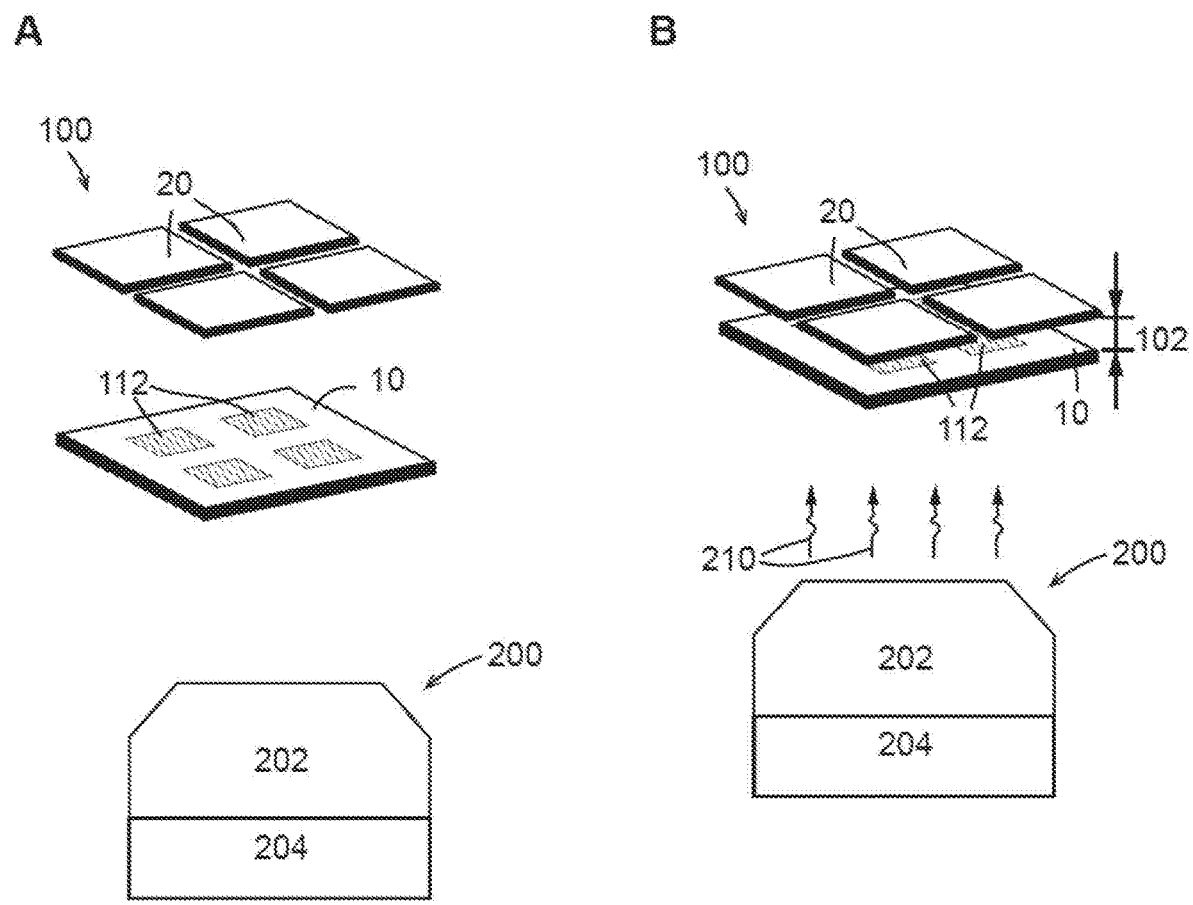
FIG. 6 shows perspective views of another embodiment of the present invention, where there are multiple sample contact areas on the plates, allowing the processing and analysis of multiple samples.

FIG. 6 shows perspective views of another embodiment of the present invention, where there are multiple sample contact areas on the plates, allowing the processing and analysis of multiple samples. As shown in panels (A) and (B) of FIG. 3, the thermal cycler system of the present invention comprises a sample holder 100 and a thermal control unit 200; the sample holder 100 comprises a first plate 10, a plurality of second plates 20, and a plurality of spacing mechanisms (not shown); the thermal control unit 200 comprises a heating source 202 and a controller 204.

Referring to panel (A) of FIG. 6, one or both of the plates (e.g. the first plate 10) comprises a plurality of sample contact areas (not marked). In some embodiments, one or both of the plates (e.g. the first plate 10) comprises a plurality of heating layers 112. Panel (A) of FIG. 4 shows the sample holder 100 in an open configuration, in which the first plate 10 and the second plates 20 are partially or entirely separated apart, allowing the deposition of one or more samples on one or both of the plates. In the open configuration, the spacing between the first plate 10 and the second plates 20 are not regulated by the spacing mechanisms.

Panel (B) of FIG. 6 shows the sample holder 100 in a closed configuration, in which the inner surfaces of the two plates face each other and the spacing 102 between the two plates are regulated by the spacing mechanism (not shown). If one or more samples have been deposited on the plates, the plates are configured to compress each sample into a layer, the thickness of the layer is regulated by the spacing mechanism.

As shown in panel (B) of FIG. 6, a plurality of second plates 20 is used to cover part of the first plate 10. For example, each second plate 20 covers a single sample contact area, onto which a sample is deposited. A spacing mechanism is present for each sample contact area and the spacing mechanisms have different heights, resulting in different spacing 102 for each sample contact area and for different thickness for each sample layer. For example, the spacing mechanism is pillar shaped spacers; each sample contact area has a set of spacers having a uniform height; different sets of spacers have the same or different heights, resulting in same or different sample layer thickness for the different samples.

Referring to panels (A) and (B) of FIG. 6, in some embodiments, the controller 204 directs the heating source 202 to project an electromagnetic wave 210 to the first plate 10 (and thus the heating layer 112), where the electromagnetic wave 210 is absorbed by the heating layer 112 and converted to heat, resulting in change of temperature in the samples. in some embodiments, when there are multiple sample contact areas, multiple samples are processed and analyzed. For example, in certain embodiments each of the sample is a pre-mixed PCR reaction medium having different components. One sample holder 100 is used to test different conditions for amplifying the same nucleotide and/or amplifying different nucleotides with the same or different conditions.

Exemplary Embodiments

A1. A device for rapidly changing temperature of a thin fluidic sample layer, comprising: a first plate, a second plate, and a heating layer, wherein:
  i. the heating layer is on one of the plates,
  ii. each of the plates comprises, on its respective surface, a sample contact area for contacting a fluidic sample; and
  iii. the plates have a configuration for rapidly changing temperature of the sample, in which:
    a. the sample contact areas face each other and are significant parallel,
    b. the average spacing between the contact areas is equal to or less than 200 microns,
    c. the two plates regulate (or confine) at least part of the sample into a layer of highly uniform thickness and substantially stagnant relative to the plates,
    d. the heating layer is near the at least part of the sample of uniform thickness,
    e. the area of the at least part of the sample and the heating layer are substantially larger than the uniform thickness.

A2. The device of embodiment A1, wherein the heating layer comprises a disk-coupled dots-on-pillar antenna (D2PA) array, silicon sandwich, graphene, back materials, superlattice or other plasmonic materials, other a combination thereof.

A3. The device of embodiment A1, wherein the heating layer comprises carbon or black nanostructures or a combination thereof.

A4. The device of any of embodiments A1-A3, wherein the heating layer is configured to absorb radiation energy.

A5. The device of any of embodiments A1-A4, wherein the heating layer is configured to radiate energy in the form of heat after absorbing radiation energy.

A6. The device of any of embodiments A1-A5, wherein the heating layer is positioned underneath the sample layer and in direct contact with the sample layer.

A7. The device of any of embodiments A1-A6, wherein the heating layer is configured to absorbing electromagnetic waves selected from the group consisting of: radio waves, microwaves, infrared waves, visible light, ultraviolet waves, X-rays, gamma rays, and thermal radiation.

A8. The device of any of embodiments A1-A7, wherein at least one of the plates does not block the radiation that the heating layer absorbs.

A9. The device of any of embodiments A1-A8, wherein one or both of the plates have low thermal conductivity.

A10. The device of any of embodiments A1-A9, wherein the uniform thickness of the sample layer is regulated by one or more spacers that are fixed to one or both of the plates.

A11. The device of any of embodiments A1-A10, wherein the sample is a pre-mixed polymerase chain reaction (PCR) medium.

A12. The device of embodiment A11, wherein the device is configured to facilitate PCR assays for changing temperature of the sample according to a predetermined program.

A13. The device of any of embodiments A1-A12, wherein the device is configured to conduct diagnostic testing, health monitoring, environmental testing, and/or forensic testing.

A14. The device of any of embodiments A1-A13, wherein the device is configured to conduct DNA amplification, DNA quantification, selective DNA isolation, genetic analysis, tissue typing, oncogene identification, infectious disease testing, genetic fingerprinting, and/or paternity testing.

A15. The device of any of embodiment A1-A14, wherein the sample layer is laterally sealed to reduce sample evaporation.

B1. A system for rapidly changing temperature of a thin fluidic sample layer, comprising: a first plate, a second plate, a heating layer, and a heating source, wherein:
  i. the heating layer is on one of the plates;
  ii. the heating source is configured to radiate electromagnetic waves that the heating layer absorbs significantly;
  iii. each of the plates comprises, on its respective surface, a sample contact area for contacting a fluidic sample; and
  iv. the plates have a configuration for rapidly changing temperature of the sample, in which:
    a. the sample contact areas face each other and are significant parallel,
    b. the average spacing between the contact areas is equal to or less than 200 μm, c. the two plates confine at least part of the sample into a layer of highly uniform thickness and substantially stagnant relative to the plates,
d. the heating layer is near the at least part of the sample of uniform thickness,
e. the area of the at least part of the sample and the heating layer are substantially larger than the uniform thickness.

B2. The system of embodiment B1, wherein the heating layer comprises a disk-coupled dots-on-pillar antenna (D2PA) array, silicon sandwich, graphene, superlattice or other plasmonic materials, other a combination thereof.

B3. The system of embodiment B1, wherein the heating layer comprises carbon or black nanostructures or a combination thereof.

B4. The system of any of embodiments B1-B3, wherein the heating layer is configured to absorb at least 80% of the radiation energy from the electromagnetic waves from the heating source.

B5. The system of any of embodiments B1-B4, wherein the heating layer is configured to radiate energy in the form of heat after absorbing radiation energy.

B6. The system of any of embodiments B1-B5, wherein the heating layer is positioned underneath the sample layer and in direct contact with the sample layer.

B7. The system of any of embodiments B1-B6, wherein the heating layer is configured to absorbing electromagnetic waves selected from the group consisting of: radio waves, microwaves, infrared waves, visible light, ultraviolet waves, X-rays, gamma rays, and thermal radiation.

B8. The system of any of embodiments B1-B7, wherein at least one of the plates does not block the radiation from the heating source.

B9. The system of any of embodiments B1-B8, wherein one or both of the plates have low thermal conductivity.

B10. The system of any of embodiments B1-B9, wherein the uniform thickness of the sample layer is regulated by one or more spacers that are fixed to one or both of the plates.

B11. The system of any of embodiments B1-B10, wherein the sample is a pre-mixed polymerase chain reaction (PCR) medium.

B12. The system of embodiment B11, wherein the system is configured to facilitate PCR assays for changing temperature of the sample according to a predetermined program.

B13. The system of any of embodiments B1-B12, wherein the system is configured to conduct diagnostic testing, health monitoring, environmental testing, and/or forensic testing.

B14. The system of any of embodiments B1-B15, wherein the system is configured to conduct DNB amplification, DNB quantification, selective DNB isolation, genetic analysis, tissue typing, oncogene identification, infectious disease testing, genetic fingerprinting, and/or paternity testing.

B15. The system of any of embodiments B1-B14, wherein the sample layer is laterally sealed to reduce sample evaporation.

B16. The system of any of embodiments B1-B15, further comprising a controller, which is configured to control the presence, intensity, wavelength, frequency, and/or angle of the electromagnetic waves.

B17. The system of any of embodiments B1-B16, further comprising a thermometer, which is configured to measure the temperature at or in proximity of the sample contact area and send a signal to the controller based on the measured temperature.

B18. The system of embodiment B17, wherein the thermometer is selected from the group consisting of: fiber optical thermometer, infrared thermometer, liquid crystal thermometer, pyrometer, quartz thermometer, silicon bandgap temperature sensor, temperature strip, thermistor, and thermocouple.

C1. A system for facilitating a polymerase chain reaction (PCR) by rapidly changing temperature of a thin fluidic PCR sample layer, comprising:
a first plate, a second plate, a heating layer, a heating source, and a controller wherein:
i. the heating layer is on one of the plates;
ii. the heating source is configured to radiate electromagnetic waves that the heating layer absorbs significantly;
iii. each of the plates comprises, on its respective surface, a sample contact area for contacting a fluid PCR sample, which is a pre-mixed PCR medium;
iv. the controller is configured to control the heating source and rapidly change the temperature of the sample according to a predetermined program; and
v. the plates have a configuration for rapidly changing temperature of the sample, in which:
(a) the sample contact areas face each other and are significant parallel,
(b) the average spacing between the contact areas is equal to or less than 200 μm,
(c) the two plates confine at least part of the sample into a layer of highly uniform thickness and substantially stagnant relative to the plates,
(d) the heating layer is near the at least part of the sample of uniform thickness, and
(e) the area of the at least part of the sample and the heating layer are substantially larger than the uniform thickness.

C2. The system of embodiment C1, wherein the controller is configured to control the present, intensity, wavelength, frequency, and/or angle of the electromagnetic waves from the heating source.

C3. The system of embodiment C1 or C2, wherein the heating source and the heating layer are configured that the electromagnetic waves cause an average ascending temperature rate ramp of at least 10° C./s; and the removal of the electromagnetic waves results in an average descending temperature rate ramp of at least 5° C./s.

C4. The system of any of embodiments C1-C2, wherein the heating source and the heating layer are configured to create an average ascending temperature rate ramp of at least 10° C./s and an average descending temperature rate ramp of at least 5° C./s.

C5. The system of any of embodiments C1-C2, wherein the heating source and the heating layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

C6. The system of any of embodiments C1-C5, wherein the PCR sample comprises: template DNA, primer DNA, cations, polymerase, and buffer.

D1. A method for rapidly changing temperature of a thin fluidic sample layer, comprising:
i. providing a first plate a second plate, each of the plates comprising, on its respective inner surface, a sample contact area;
ii. providing a heating layer and a heating source, wherein the heating layer is on one of the plates, and the heating source is configured to radiate electromagnetic waves that the heating layer absorbs significantly;

iii. depositing a fludic sample on one or both of the plates;
iv. pressing the plates into a closed configuration, in which:
   (a) the sample contact areas face each other and are significant parallel,
   (b) the average spacing between the contact areas is equal to or less than 200 µm,
   (c) the two plates confine at least part of the sample into a layer of highly uniform thickness and substantially stagnant relative to the plates;
   (d) the heating layer is near the at least part of the sample of uniform thickness,
   (e) the area of the at least part of the sample and the heating layer are substantially larger than the uniform thickness; and
v. changing and maintaining the temperature of the sample layer by changing the presence, intensity, wavelength, frequency, and/or angle of the electromagnetic waves from the heating source.

D2. The method of embodiment D1, wherein the step of pressing the plates into a closed figuration comprises pressing the plates with an imprecise pressing force.

D3. The method of embodiment D1 or D2, wherein the step of pressing the plates into a closed figuration comprises pressing the plates directedly with human hands.

D4. The method of any of embodiments D1-D3, wherein the layer of highly uniform thickness has a thickness variation of less than 10%.

D5. The method of any of embodiments D1-D4, wherein the heating layer comprises a disk-coupled dots-on-pillar antenna (D2PA) array, silicon sandwich, graphene, superlattice or other plasmonic materials, other a combination thereof.

D6. The method of any of embodiments D1-D5, wherein the heating layer comprises carbon or black nanostructures or a combination thereof.

D7. The method of any of embodiments D1-D6, wherein the heating layer is configured to absorb at least 80% of the radiation energy from the electromagnetic waves from the heating source.

D8. The method of any of embodiments D1-D7, wherein the heating layer is configured to radiate energy in the form of heat after absorbing radiation energy.

D9. The method of any of embodiments D1-D8, wherein the heating layer is positioned underneath the sample layer and in direct contact with the sample layer.

D10. The method of any of embodiments D1-D9, wherein the heating layer is configured to absorbing electromagnetic waves selected from the group consisting of: radio waves, microwaves, infrared waves, visible light, ultraviolet waves, X-rays, gamma rays, and thermal radiation.

D11. The method of any of embodiments D1-D10, wherein at least one of the plates does not block the radiation from the heating source.

D12. The method of any of embodiments D1-D11, wherein one or both of the plates have low thermal conductivity.

D13. The method of any of embodiments D1-D12, wherein the uniform thickness of the sample layer is regulated by one or more spacers that are fixed to one or both of the plates.

D14. The method of any of embodiments D1-D13, wherein the sample is a pre-mixed polymerase chain reaction (PCR) medium.

D15. The method of embodiment D14, wherein the method is used to facilitate PCR assays for changing temperature of the sample according to a predetermined program.

D16. The method of any of embodiments D1-D15, wherein the method is used to conduct diagnostic testing, health monitoring, environmental testing, and/or forensic testing.

D17. The method of any of embodiments D1-D16, wherein the method is used to conduct DNB amplification, DNB quantification, selective DNB isolation, genetic analysis, tissue typing, oncogene identification, infectious disease testing, genetic fingerprinting, and/or paternity testing.

D18. The method of any of embodiments D1-D17, wherein the sample layer is laterally sealed to reduce sample evaporation.

D19. The method of any of embodiments D1-D18, wherein the heating source is controlled by a controller, which is configured to control the presence, intensity, wavelength, frequency, and/or angle of the electromagnetic waves.

D20. The method of any of embodiments D1-D19, wherein the controller is configured to receive signals from a thermometer, which is configured to measure the temperature at or in proximity of the sample contact area and send a signal to the controller based on the measured temperature.

D21. The method of embodiment D20, wherein the thermometer is selected from the group consisting of: fiber optical thermometer, infrared thermometer, liquid crystal thermometer, pyrometer, quartz thermometer, silicon band-gap temperature sensor, temperature strip, thermistor, and thermocouple.

E1. A method for facilitating a polymerase chain reaction (PCR) by rapidly changing temperatures in a fluidic PCR sample, comprising:
   i. providing a first plate a second plate, each of the plates comprising, on its respective inner surface, a sample contact area;
   ii. providing a heating layer, a heating source and a controller, wherein the heating layer is on one of the plates, and the heating source is configured to radiate electromagnetic waves that the heating layer absorbs significantly;
   iii. depositing a fluidic PCR sample on one or both of the plates;
   iv. pressing the plates into a closed configuration, in which:
      (a) the sample contact areas face each other and are significant parallel,
      (b) the average spacing between the contact areas is equal to or less than 200 µm,
      (c) the two plates confine at least part of the PCR sample into a layer of highly uniform thickness and substantially stagnant relative to the plates;
      (d) the heating layer is near the at least part of the PCR sample of uniform thickness,
      (e) the area of the at least part of the sample and the heating layer are substantially larger than the uniform thickness; and
   v. using the controller to control the heating source to conduct a PCR by changing and maintaining the temperature of the PCR sample layer according to a predetermined program, wherein when the temperatures are changed, the heating source creates an average ascending temperature rate ramp of at least 10° C./s and an average descending temperature rate ramp of at least 5° C./s during the PCR.

E2. The method of embodiment E1, wherein changing and maintaining the temperature of the PCR sample layer is achieved by adjusting the intensity, wavelength, frequency, and/or angle of the electromagnetic waves from the heating source.

E3. The system of any of embodiments E1-E2, wherein the heating source and the heating layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

E4. The method of any of embodiments E1-E3, wherein the PCR sample comprises: template DNA, primer DNA, cations, polymerase, and buffer.

NN1 A device for rapidly changing temperature of a thin fluidic sample layer, comprising: a first plate, and a second plate, wherein:
   i. each of the plates comprises, on its respective surface, a sample contact area for contacting a fluidic sample; and
   ii. the plates have a configuration for rapidly changing temperature of the sample, in which:
      a. the sample contact areas face each other and are significant parallel,
      b. the average spacing between the contact areas is equal to or less than 200 microns,
      c. the two plates regulate (or confine) at least part of the sample into a layer of highly uniform thickness and substantially stagnant relative to the plates,
      d. the heating layer is near the at least part of the sample of uniform thickness,
      e. the area of the at least part of the sample and the heating layer are substantially larger than the uniform thickness.

Additional Exemplary Embodiments

1. Device for Rapidly Changing a Sample Temperature

AA1 A device for rapidly changing a fluidic sample temperature, comprising:
a first plate, a second plate, and a heating layer, wherein:
   iv. the plates are movable relative to each other into different configurations;
   v. each of the plates has, on its respective inner surface, a sample contact area for contacting a fluidic sample, and
   vi. the heating layer is configured to heat the fluidic sample;
      wherein the heating layer is (a) on (either the inner or outer surface) or inside one of the plates, and (b) capable of being heated by a heating source, wherein the heating source delivers heat energy to the heating layer optically, electrically, by radio frequency (RF) radiation, or a combination thereof;
      wherein at least a part of a heating area of the heating layer overlaps with the sample area,
      wherein one of the configurations is an open configuration, in which: the two plates are partially or completely separated apart and the average spacing between the plates is at least 300 um; and
      wherein another of the configurations is a closed configuration which is configured after the fluidic sample is deposited on one or both of the sample contact areas in the open configuration; and in the closed configuration: at least part of the sample is compressed by the two plates into a layer, wherein the average sample thickness is 200 um or less.

AA2.1 A device for rapidly changing temperature of a fluidic sample, comprising: a sample holder and a heating layer, wherein:
   iv. the sample holder comprises a first plate and a second plate, wherein each of the plates comprises, on its respective surface, a sample contact area for contacting the fluidic sample;
   v. the first plate and the second plate are configured to confine the fluidic sample into a layer of highly uniform thickness of 0.1-200 um and substantially stagnant relative to the plates; and
   vi. the heating layer: (1) has a thickness of less than 1 mm, (2) has an area that is substantially less than the area of either the first or the second plate, and (3) is configured to convert energy from electromagnetic waves into heat to raise the temperature of at least part of the fluidic sample in the layer of uniform thickness.

AA2.2 A device for rapidly changing temperature of a fluidic sample, comprising: a sample holder and a heating layer, wherein:
   i. the sample holder comprises a first plate and a second plate, wherein each of the plates comprises, on its respective surface, a sample contact area for contacting the fluidic sample;
   ii. the first plate and the second plate are configured to confine at least part of the sample into a layer of highly uniform thickness of 0.1-200 um and substantially stagnant relative to the plates,
   iii. the first plate has a thickness of 500 um or less, and the second plate has a thickness of 5 mm or less; and
   iv. the heating layer has a thickness of less than 1 mm and an area of less than 100 mm$^2$ and is configured to convert energy from electromagnetic waves into heat to raise the temperature of the at least part of the fluidic sample in the layer of uniform thickness.

AA2.3 A device for rapidly changing temperature of a fluidic sample, comprising:
a sample holder and a heating layer, wherein:
   i. the sample holder comprises a first plate and a second plate, wherein each of the plates comprises, on its respective surface, a sample contact area for contacting the fluidic sample;
   ii. the first plate and the second plate are configured to confine at least part of the sample into a layer of highly uniform thickness of 0.1-200 um and substantially stagnant relative to the plates,
   iii. the first plate has a thickness of 500 um or less, and the second plate has a thickness of 5 mm or less; and
   iv. the heating layer: (1) has a thickness of less than 1 mm, (2) has an area of less than 100 mm$^2$ that is substantially less than the area of either the first or the second plate, and (3) is configured to convert energy from electromagnetic waves into heat to raise the temperature of at least part of the fluidic sample in the layer of uniform thickness.

AA3 A device for rapidly changing temperature of a fluidic sample, comprising:
a sample holder and a heating layer, wherein:
   i. the sample holder comprises a first plate and a second plate, wherein each of the plates comprises, on its respective surface, a sample contact area for contacting the fluidic sample;
   ii. the first plate and the second plate are configured to confine at least part of the sample into a layer of highly uniform thickness of 500 um or less and substantially stagnant relative to the plates, iii. the first plate is in contact with the heating layer and has a thickness of 1 um or less, and the second plate is not in contact with the heating layer and has a thickness of 5 mm or less; and iv. the heating layer is configured to convert energy from electromagnetic waves into heat to raise the temperature of the at least part of the fluidic sample in the layer of uniform thickness, has an absorption coefficient of 50% or higher, and has a thickness of less than 3 mm.

AA4 A device for rapidly changing temperature of a fluidic sample, comprising:

a sample holder and a heating layer, wherein:

i. the sample holder comprises a first plate and a second plate, wherein each of the plates comprises, on its respective surface, a sample contact area for contacting the fluidic sample;

ii. the first plate and the second plate are configured to confine at least part of the sample into a layer of highly uniform thickness of 500 um or less and substantially stagnant relative to the plates, iii. the first plate is in contact with the heating layer and has a thickness of 1 um or less, and the second plate is not in contact with the heating layer and has a thickness of 0.1-2 mm; and iv. the heating layer is configured to convert energy from electromagnetic waves into heat to raise the temperature of the at least part of the fluidic sample in the layer of uniform thickness, has an absorption coefficient of 60% or higher, and has a thickness of less than 2 mm.

AA5 A device for rapidly changing temperature of a fluidic sample, comprising:

a sample holder and a heating layer, wherein:

i. the sample holder comprises a first plate and a second plate, wherein each of the plates comprises, on its respective surface, a sample contact area for contacting the fluidic sample;

ii. the first plate and the second plate are configured to confine at least part of the sample into a layer of highly uniform thickness of 500 um or less and substantially stagnant relative to the plates, iii. the first plate is in contact with the heating layer and has a thickness of 100 um or less, and the second plate is not in contact with the heating layer and has a thickness of 0.1-2 mm; and iv. the heating layer is configured to convert energy from electromagnetic waves into heat to raise the temperature of the at least part of the fluidic sample in the layer of uniform thickness, has an absorption coefficient of 70% or higher, and has a thickness of less than 2 mm.

AA6.1 The device of any prior AA embodiments, wherein the heating layer is on the inner surface of one of the plates.

AA6.2 The device of any prior AA embodiments, wherein the heating layer is on the outer surface of one of the plates.

AA6.3 The device of any prior AA embodiments, wherein the heating layer inside one of plates.

AA6.4 The device of any prior AA embodiments, wherein the heating layer is in contact with at least one of the plates.

AA6.5 The device of any prior AA embodiments, wherein the heating layer is not in contact with any of the plates.

AA6.6 The device of any prior AA embodiments, wherein the heating layer is in contact with the sample when the plates are in the closed configuration.

AA7. The device of any prior AA embodiments, wherein the heating layer is made from a single material or compound materials.

AA7.1 The device of any prior AA embodiments, wherein the heating layer comprises semiconductors or metallic materials with high absorbing surfaces.

AA7.2 The device of any prior AA embodiments, wherein the heating layer comprises Silicon, Ge, InP, GaAs, CdTe, CdS, aSi, metal including Au, A1, Ag, Ti, carbon coated A1, black painted A1, carbon (graphene, nanotube, nanowire) or a combination thereof.

AA7.3 The device of any prior AA embodiments, wherein the heating layer is acting as the fast heating conductive layer comprises Silicon, Ge, InP, GaAs, CdTe, CdS, aSi, metal including Au, Al, Ag, Ti, carbon coated A1, black painted A1, carbon (graphene, nanotube, nanowire) or a combination thereof.

AA8 The device of any prior AA embodiments, wherein the part of the heating area that overlaps the sample area is less than 1%, 5%, 10%, 20%, 30%, 40%, 50%, 60%, 70%, 80%, 90%, 95%, or 99% of the sample area, or in a range between any of the two values.

AA8.1 The device of any prior AA embodiments, wherein the part of the heating area that overlaps the sample area is less than 0.1 $mm^2$, 0.5 $mm^2$, 1 $mm^2$, 5 $mm^2$, 10 $mm^2$, 25 $mm^2$, 50 $mm^2$, 75 $mm^2$, 1 $cm^2$ (square centimeter), 2 $cm^2$, 3 $cm^2$, 4 $cm^2$, 5 $cm^2$, 10 $cm^2$, or in a range between any of the two values.

AA9. The device of any prior AA embodiments, wherein the absorption coefficient of the heating layer is more than 30%, 40%, 50%, 60%, 70%, 80%, 90%, or in a range between any of the two values.

AA9.1. The device of any prior AA embodiments, wherein the absorption coefficient of the heating layer is more than 60%, 70%, 80%, 90%, or in a range between any of the two values.

AA9.2. The device of any prior AA embodiments, wherein the absorption coefficient of the heating layer is more than 60%.

AA10. The device of any prior AA embodiments, wherein the heating layer has an absorption wavelength range that is 100 nm to 300 nm, 400 nm to 700 nm (visible range), 700 nm to 1000 nm (IR range), 1 um to 10 um, 10 um to 100 um, or in a range between any of the two values.

AA11. The device of any prior AA embodiments, wherein the heating layer has a thickness equal to or less than 3 mm, 2 mm, 1 mm, 750 um, 500 um, 250 um, 100 um, 50 um, 25 um, 10 um, 500 nm, 200 nm, 100 nm, or 50 nm, or in a range between any of the two values.

AA12. The device of any prior AA embodiments, wherein the heating layer has an area of 0.1 $mm^2$ or less, 1 $mm^2$ or less, 10 $mm^2$ or less, 25 $mm^2$ or less, 50 $mm^2$ or less, 75 $mm^2$ or less, 1 $cm^2$ (square centimeter) or less, 2 $cm^2$ or less, 3 $cm^2$ or less, 4 $cm^2$ or less, 5 $cm^2$ or less, 10 $cm^2$ or less, or in a range between any of the two values.

AA13. The device of any prior AA embodiments, wherein the first plate has a thickness equal to or less than 500 um, 200 um, 100 um, 50 um, 25 um, 10 um, 5 um, 2.5 um, 1 um, 500 nm, 400 nm, 300 nm, 200 nm, or 100 nm, or in a range between any of the two values.

AA13.1. The device of any prior AA embodiments, wherein the first plate has a thickness equal of 10-200 um.

AA14. The device of any prior AA embodiments, wherein the second plate has a thickness equal to or less than 5 mm, 4 mm, 3 mm, 2 mm, 1 mm, 750 um, 500 um, 250 um, 100 um, 75 um, 50 um, or 25 um, or in a range between any of the two values.

AA14.1. The device of any prior AA embodiments, wherein the second plate has a thickness equal of 10-1000 um.

AA15. The device of any prior AA embodiments, wherein the sample layer has a highly uniform thickness.

AA15.1 The device of any prior AA embodiments, wherein the sample layer has a thickness of equal to or less than 100 um, 50 um, 20 um, 10 um, 5 um, 1 um, 500 nm, 400 nm, 300 nm, 200 nm, or 100 nm, or in a range between any of the two values.

AA15.2. The device of any prior AA embodiments, wherein the sample layer has a thickness of 1-100 um.

AA16. The device of any prior AA embodiments, wherein the area of at least one of the plate is 1 mm$^2$ or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1000 cm$^2$ or less, 5000 cm$^2$ or less, 10,000 cm$^2$ or less, 10,000 cm$^2$ or less, or in a range between any two of these values.

AA17.1 The device of any prior AA embodiments, wherein the area of at least one of the plates is in the range of 500 to 1000 mm$^2$; or around 750 mm$^2$.

AA18. The device of any prior AA embodiments, further comprising spacers that are configured to regulate the thickness of the sample layer.

AA18.1 The device of any prior AA embodiments, wherein the spacers are fixed on either one or both of the plates.

AA18.2 The device of any prior AA embodiments, wherein the spacers are fixed on the inner surface of either one or both of the plates.

AA18.3 The device of any prior AA embodiments, wherein the spacers have a uniform height.

AA18.4 The device of any prior AA embodiments, wherein at least one of the spacers is inside the sample contact area.

AA18.5 The device of any prior AA embodiments, wherein the thickness of the sample layer is the same as the height of the spacers.

AA19 The device any prior AA embodiments, wherein one or both plates are flexible.

AA20. The device of any prior AA embodiments, further comprising sealing structures that are attached to either one or both of the contact and second plates, wherein the sealing structures are configured to limit the evaporation of liquid inside the device.

AA21. The device of any prior AA embodiments, further comprising a clamping structure that is attached to either one or both of the first and second plates, wherein the clamp structure is configured to hold the device and regulate the thickness of the sample layer during the heating of the device.

AA22 The device of any prior AA embodiments, wherein the second plate is transparent for an electromagnetic wave from the sample.

AA23. The device of any prior AA embodiments, wherein the sample holder and the heating layer are connected by a thermal coupler.

AA24. The device of any prior AA embodiments, wherein the areas of the at least part of the sample and the heating layer are substantially larger than the uniform thickness.

AA25. The device of any prior AA embodiments, wherein the heating layer is configured to absorb electromagnetic waves selected from the group consisting of: radio waves, microwaves, infrared waves, visible light, ultraviolet waves, X-rays, gamma rays, and thermal radiation.

AA26. The device of any prior AA embodiments, wherein the sample is a pre-mixed polymerase chain reaction (PCR) medium.

AA27. The device of any prior AA embodiments, wherein the sample layer is laterally sealed to reduce sample evaporation.

AA28. The device of any prior AA embodiments, wherein the area of the radiation is smaller than the area of radiation absorption pad; The area of the radiation absorption pad is less than the area of sample liquid area; The area of sample liquid area is less than the first and second plate size.

AA29. The device of any prior AA embodiments, wherein the fluidic sample comprises a processed or unprocessed bodily fluid.

AA30. The device of any prior AA embodiments, wherein the fluidic sample comprises amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled condensate, or a mixture thereof.

AA31. The device of any prior AA embodiments, wherein the fluidic sample comprises nucleic acids or proteins, or a mixture thereof.

AA32. The device of any prior AA embodiments, wherein the fluidic sample comprises DNA or RNA, or a mixture thereof.

2. Apparatus with Heating Source

BB1. An apparatus for rapidly changing temperature of a fluidic sample, comprising:
 i. a holder that can hold a device of any AA embodiments; and
 ii. a heating source that is configured to supply energy to the heating layer; and
 iii. a controller that is configured to control the heating source.

BB1.1 The apparatus of any prior BB embodiments, wherein the heating source is configured to radiate electromagnetic waves in a range of wavelength that the heating layer has an absorption coefficient of 50% or higher.

BB2. The apparatus of any prior BB embodiments, wherein the heating source comprises one or an array of light-emitting diodes (LEDs), one or an array of lasers, one or an array of lamps, or a combination of thereof.

BB2.1. The apparatus of any prior BB embodiments, wherein the heating source comprises halogen lamp, halogen lamp with reflector, LED with focusing lens, laser with focusing lens, halogen lamp with coupling optical fiber, LED with coupling optical fiber, laser with coupling optical fiber.

BB3. The apparatus of any prior BB embodiments, wherein the wavelength is 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 um, 10 um, 25 um, 50 um, 75 um, or 100 um, or in a range between any of the two values.

BB3.1 The apparatus of any prior BB embodiments, wherein the wavelength of the electromagnetic waves is 100 nm to 300 nm, 400 nm to 700 nm (visible range), 700 nm to 1000 nm (IR range), 1 um to 10 um, 10 um to 100 um, or in a range between any of the two values.

BB4. The apparatus of any prior BB embodiments, further comprising a heat sink that is configured to absorb at least part of the heat radiated from the sample holder and/or the heating source.

BB4.1 The apparatus of any prior BB embodiments, wherein the heat sink is chamber that at least partially encloses the device.

BB4.2. The apparatus of any prior BB embodiments, wherein the chamber comprises a lower aperture configured to allow passage of electromagnetic waves from the heating source to the heating layer, and an upper aperture configured to allow imaging of the sample.

BB5. The apparatus of any prior BB embodiments, wherein the sample holder is heated optically, electrically, by RF, or a combination of thereof.

BB6. An apparatus for rapidly changing temperature of a fluidic sample, comprising:
    i. a device of any AA embodiments; and
    ii. a heat sink that is configured to absorb at least part of the heat radiated from the sample holder and/or the heating source.

BB7. The apparatus of any prior BB embodiments, wherein the heat sink is a chamber that at least partially encloses the device, wherein the chamber comprises a radiation aperture configured to allow passage of electromagnetic waves from a heating source to the heating layer, and an optical aperture configured to allow imaging of the sample.

BB8. The apparatus of any prior BB embodiments, further comprising a cooling member attached to the chamber, wherein the cooling member is configured to reduce temperature in the chamber.

BB9. The apparatus of embodiment BB7, wherein the cooling member is a fan.

BB10. The apparatus of embodiment BB7, wherein the cooling member is a Peltier cooler.

BB11. The apparatus of any BB embodiments, wherein the chamber has a non-reflective inner surface.

BB11.1 The apparatus of any BB embodiments, wherein the chamber has an inner surface made of black metal.

BB12. The apparatus of any BB embodiments, wherein the device is suspended (i.e. has minimum) thermal conduction contact with the chamber wall.

3. System for Observing an Optical Signal from the Sample and Rapidly Changing a Sample Temperature CC1. A system for rapidly changing temperature of a fluidic sample, comprising:
    i. a device of any AA embodiments or an apparatus of any BB embodiments; and
    ii. a signal sensor that is configured to senses a signal from the sample on the device.

CC2. The system of any prior CC embodiments, wherein the signal sensor is an optical sensor that is configured to image the fluidic sample.

CC2.1 The system of any prior CC embodiments, wherein the optical sensor is a photodetector, camera, or a device capable of capturing images of the fluidic sample.

CC3. The system of any prior CC embodiments, wherein the signal sensor is an electrical sensor that is configured to detect electrical signals from the device.

CC4 The system of any prior CC embodiments, wherein the signal sensor is a mechanical sensor that is configured to detect mechanical signals from the device.

CC5 The system of any prior CC embodiments, wherein the signal sensor is configured to monitor the amount of an analyte in the sample.

CC6. The system of any prior CC embodiments, wherein signal sensor is outside the chamber and receive optical signals from the sample through an optical aperture on the chamber.

CC7. The system of any CC embodiment, further comprising a thermal coupler bound to the heating layer.

CC8. The system of any prior CC embodiments, further comprising a thermostat that monitor the temperature of the heating layer.

CC9. The system of any prior CC embodiments, further comprising a temperature monitoring dye that is configured to facilitate monitoring the temperature of the sample in the device.

CC9.1. The system of any prior CC embodiments, wherein the temperature monitoring dye is in liquid form.

CC9.2 The system of any prior CC embodiments, wherein the temperature monitoring dye comprises LDS 688, LDS 698, LDS 950, LD 390, LD 423, LD 425, or IR 144, or a combination thereof.

4. Various Embodiments

DD1. The device, apparatus, or system of any prior embodiments, wherein:
    i. there are spacers that are fixed on one of both of the plates, wherein at least one of the spacers is in the sample contact area;
    ii. the sample layer has a thickness of 0.1-200 um;
    iii. the first plate is in contact with the heating layer and has a thickness of 500 um or less, and the second plate is not in contact with the heating layer and has a thickness of 5 mm or less; and
    iv. the heating layer: (1) has a thickness of less than 1 mm, (2) has an area of less than 100 $mm^2$ that is substantially less than the area of either the first or the second plate, and (3) is configured to convert energy from electromagnetic waves into heat to raise the temperature of at least part of the fluidic sample in the layer of uniform thickness.

DD2. The device, apparatus, or system of any prior embodiments, wherein:
    i. the heating layer is on the inner surface of the first plate and in contact with the sample when the plates are in the closed configuration;
    ii. the heating layer is made from silicon; and
    iii. there is a chamber that encloses the sample holder and the chamber has a non-reflective inner surface.

DD3. The device, apparatus, or system of any prior embodiments, wherein:
    i. there is a heating source that is configured to radiate electromagnetic waves in a range of wavelength that the heating layer has an absorption coefficient of 50% or higher;
    ii. there is a chamber that comprises a lower aperture configured to allow passage of electromagnetic waves from the heating source to the heating layer, and an upper aperture configured to allow imaging of the sample; and iii. there is an optical sensor that is configured to capture images of the fluidic sample in the sample holder.

5. Methods

EE1. A method for rapidly changing temperature of a fluidic sample, comprising:
  i. obtaining the system of the CC embodiments;
  ii. depositing the fluidic sample in the sample holder;
  iii. pressing the first plate and the second plate to compress at least part of the sample into a layer of uniform thickness; and
  iv. changing and maintaining the temperature of the sample layer by changing the presence, intensity, wavelength, frequency, and/or angle of the electromagnetic waves from the heating source.

EE2. The method of any prior EE embodiments, wherein changing the temperature of the sample layer comprises raising the temperature or lowering the temperature.

EE3. The method of any prior EE embodiments, further comprising imaging the sample layer with the optical sensor.

EE4. The method of any prior EE embodiments, further comprising monitoring the temperature of the sample layer and adjusting the step of changing and maintaining the temperature of the sample layer.

EE5. The method of any prior EE embodiments, wherein the step of changing and maintaining the temperature of the sample layer is conducted according to a pre-determined program.

EE6. The method of any prior EE embodiments, wherein the method is customized to facilitate polymerase chain reaction (PCR) assays for changing temperature of the sample according to a predetermined program EE7. The method of any prior EE embodiments, further comprising monitoring the amount of an analyte in the sample in real time.

6. Samples

FF1. The device, apparatus, system or method of any prior embodiments, wherein the sample comprises nucleic acids.

FF1.1. The device, apparatus, system or method of any prior embodiments, wherein the sample comprises DNA.

FF1.2 The device, apparatus, system or method of any prior embodiments, wherein the sample comprises RNA.

FF1.3 The device, apparatus, system or method of any prior embodiments, wherein the sample comprises DNA or RNA molecule, or a DNA/RNA hybrid, or mixtures of DNA and/or RNA.

FF1.4 The device, apparatus, system or method of any prior embodiments, wherein the sample comprises genomic or chromosomal DNA, plasmid DNA, amplified DNA, cDNA, total RNA, mRNA and small RNA.

FF1.5 The device, apparatus, system or method of any prior embodiments, wherein the sample comprises natural DNA and/or RNA molecule, or synthetic DNA and/or RNA molecule.

FF1.6 The device, apparatus, system or method of any prior embodiments, wherein the sample comprises cell-free nucleic acids, wherein "cell-free" refers to nucleic acids are not contained in any cellular structures.

FF1.7 The device, apparatus, system or method of any prior embodiments, wherein the sample comprises nucleic acids are contained within cellular structures, which include but not limited to human cells, animal cells, plant cells, bacterial cells, fungi cells, and/or viral particles.

FF1.8 The device, apparatus, system or method of any prior embodiments, wherein the sample comprises purified nucleic acids.

FF2 The device, apparatus, system or method of any prior embodiments, wherein the sample comprises proteins and/or lipids.

FF3. The device, apparatus, system or method of any prior embodiments, wherein the sample comprises reagents configured for nucleic acid amplification.

FF3.1. The device, apparatus, system or method of any prior embodiments, wherein the sample comprises a pre-mixed polymerase chain reaction (PCR) medium.

FF3.2. The device, apparatus, system or method of any prior embodiments, wherein the sample comprises reagents configured to detect nucleic acids by amplifying (generating numerous copies of) the target molecules in samples, wherein target molecule refers to a sequence, or partial sequence, of nucleic acid of interest.

FF3.3. The device, apparatus, system or method of any prior embodiments, wherein the nucleic acid amplification refers to nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

FF3.4. The device, apparatus, system or method of any prior embodiments, wherein the reagents comprise primers, deoxynucleotides (dNTPs), bivalent cations (e.g. $Mg^{2+}$), monovalent cation (e.g. $K^+$), buffer solutions, enzymes, or reporters, or any combination or mixture thereof.

FF3.5. The device, apparatus, system or method of any prior embodiments, wherein the reagents are either in the dry form on the inner surface of the first or the second plate or both, or in a liquid form encased in, embedded in, or surrounded by, a material that melts with increasing temperatures, such as, for example, paraffin.

FF3.6. The device, apparatus, system or method of any prior embodiments, wherein primers comprise one or more pairs of forward and reverse primers.

FF3.7. The device, apparatus, system or method of any prior embodiments, wherein the reagents comprise DNA-dependent polymerase, or RNA-dependent DNA polymerase, or DNA-dependent RNA polymerase.

FF3.8. The device, apparatus, system or method of any prior embodiments, wherein the reagents comprise "reporters" that refer to any tag, label, or dye that can bind to, or intercalate within, the nucleic acid molecule or be activated by byproducts of the amplification process to enable visualization of the nucleic acid molecule or the amplification process.

FF3.8.1 The device, apparatus, system or method of any prior embodiments, wherein the reports include but are not limited to fluorescent labels or tags or dyes, intercalating agents, molecular beacon labels, or bioluminescent molecules, or a combination thereof.

FF3.9. The device, apparatus, system or method of any prior embodiments, wherein the reagents comprise cell lysing reagent, which is configured to facilitate breaking down cellular structures.

FF3.9.1. The device, apparatus, system or method of any prior embodiments, wherein the cell lysing reagent includes but not limited to salts, detergents, enzymes, and other additives.

FF3.9.2. The device, apparatus, system or method of any prior embodiments, wherein the salt includes but not limited to lithium salt (e.g. lithium chloride), sodium salt (e.g. sodium chloride), potassium (e.g. potassium chloride).

FF3.9.2. The device, apparatus, system or method of any prior embodiments, wherein the detergents are ionic, including anionic and cationic, non-ionic or zwitterionic.

FF3.9.3. The device, apparatus, system or method of any prior embodiments, wherein the ionic detergent includes any detergent which is partly or wholly in ionic form when dissolved in water.

FF3.9.4. The device, apparatus, system or method of any prior embodiments, wherein anionic detergents include but not limited to sodium dodecyl sulphate (SDS) or other alkali metal alkylsulphate salts or similar detergents, sarkosyl, or combinations thereof.

FF3.10. The device, apparatus, system or method of any prior embodiments, wherein enzymes includes but not limited to lysozyme, cellulose, and proteinase.

FF3.11. The device, apparatus, system or method of any prior embodiments, wherein chelating agents include but not limited to EDTA, EGTA and other polyamino carboxylic acids, and some reducing agents, such as dithiotreitol (dTT).

FF4. The device, apparatus, system or method of any prior embodiments, wherein the sample comprises an analyte the amount of which is changed with the temperature changes.

FF5. The device, apparatus, system or method of any prior embodiments, wherein the sample comprises human bodily fluids, such as but not limited to whole blood, plasma, serum, urine, saliva, and sweat, and cell cultures (mammalian, plant, bacteria, fungi), and a combination or mixture thereof.

FF6. The device, apparatus, system or method of any prior embodiments, wherein the sample is freshly obtained, stored or treated in any desired or convenient way, for example by dilution or adding buffers, or other solutions or solvents.

FF7. The device, apparatus, system or method of any prior embodiments, wherein the sample comprises cellular structures such as but not limited to human cells, animal cells, plant cells, bacteria cells, fungus cells, and virus particles, and a combination or mixture thereof.

7. Measurement Methods

GG1. The device, apparatus, system or method of any prior embodiments, wherein an analyte in the sample is stained.

GG2. The device, apparatus, system or method of any prior GG embodiments, wherein the amount of the analyte is measured by fluorescence intensity.

GG3. The device, apparatus, system or method of any prior GG embodiments, wherein the amount of the analyte is measured by colorimetric intensity.

GG4. The device, apparatus, system or method of any prior embodiments, wherein the analyte is nucleic acid, which is stained with ethidium bromide (EB), methylene blue, SYBR green I, SYBR green II, pyronin Y, DAPI, acridine orange, or Nancy-520, or a combination thereof.

GG5. The device, apparatus, system or method of any prior embodiments, wherein the analyte is DNA, which is stained with ethidium bromide (EB), methylene blue, pyronin Y, DAPI, acridine orange, or Nancy-520, or a combination thereof, and measured with fluorescence intensity.

GG6. The device, apparatus, system or method of any prior embodiments, wherein the analyte is DNA, which is stained with ethidium bromide (EB), methylene blue, pyronin Y, DAPI, acridine orange, or Nancy-520, or a combination thereof, and measured with colorimetric intensity.

GG7. The device, apparatus, system or method of any prior embodiments, wherein the analyte is RNA, which is stained with ethidium bromide (EB), methylene blue, SYBR green II, pyronin Y, or acridine orange, or a combination thereof, and measured with fluorescence intensity.

GG8. The device, apparatus, system or method of any prior embodiments, wherein the analyte is RNA, which is stained with ethidium bromide (EB), methylene blue, SYBR green II, pyronin Y, or acridine orange, or a combination thereof, and measured with colorimetric intensity.

GG9. The device, apparatus, system or method of any prior embodiments, wherein the analyte is nucleic acid to be detected by reporters.

GG9.1. The device, apparatus, system or method of any prior embodiments, wherein the reporters include but not limited to tag, label, or dye that can bind to, or intercalate within, the nucleic acid molecule or be activated by byproducts of the amplification process to enable visualization of the nucleic acid molecule or the amplification process.

GG9.2. The device, apparatus, system or method of any prior embodiments, wherein the reporters include but are not limited to fluorescent labels or tags or dyes, intercalating agents, molecular beacon labels, or bioluminescent molecules, or a combination thereof.

GG9.3. The device, apparatus, system or method of any prior embodiments, wherein the amount of reporter is measured by colorimetric intensity and/or by fluorescence intensity.

8. Applications

HH1. The device, apparatus, system or method of any prior embodiments, wherein the device, apparatus, system or method is configured to facilitate PCR assays for changing temperature of the sample according to a predetermined program.

HH2. The device, apparatus, system or method of any prior embodiments, wherein the device, apparatus, system or method is configured to conduct diagnostic testing, health monitoring, environmental testing, and/or forensic testing.

HH3. The device, apparatus, system or method of any prior embodiments, wherein the device, apparatus, system or method is configured to conduct DNA amplification, DNA quantification, selective DNA isolation, genetic analysis, tissue typing, oncogene identification, infectious disease testing, genetic fingerprinting, and/or paternity testing.

HH4. The device, apparatus, system or method of any prior embodiments, wherein the device, apparatus, system or method is configured to conduct real time PCR.

HH5. The device, apparatus, system or method of any prior embodiments, wherein the device, apparatus, system or method is configured to conduct nucleic acid amplification.

HH5.1 The device, apparatus, system or method of any prior embodiments, wherein nucleic acid amplification includes any techniques used to detect nucleic acids by amplifying (generating numerous copies of) the target molecules in samples, wherein target molecule refers to a sequence, or partial sequence, of nucleic acid of interest.

HH6 The device, apparatus, system or method of any prior embodiments, wherein the device, apparatus, system or method is configured to conduct nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

9. Various Embodiments

JJ1. A device for assaying a thin fluidic sample layer, comprising:
a first plate, a second plate, spacers, and a clamp, wherein:
  i. the first plate and the second plate are movable relative to each other into different configurations, including an open configuration and a closed configuration;
  ii. each of the plates comprises, on its respective surface, a sample contact area for contacting a fluidic sample;
  iii. one or both of the plates comprise the spacers that are fixed to the respective plate;
  iv. the spacers have a predetermined substantially uniform height that is equal to or less than 200 microns, wherein at least one of the spacers is inside the sample contact area; and
  v. the heating layer is configured to heat the fluidic sample;
    wherein the heating layer is (a) on (either on or near the inner or outer surface) or inside one of the plates, and (b) capable of being heated by a heating source, wherein the heating source delivers heat energy to the heating layer optically, electrically, by radio frequency (RF) radiation, or a combination thereof;
  wherein in an open configuration, the two plates are partially or completely separated apart, the spacing between the plates is not regulated by the spacers, and the sample is deposited on one or both of the plates;
  wherein in a closed configuration, which is configured after the sample is deposited in the open configuration, at least a part of the sample is compressed by the two plates into a layer of substantially uniform thickness and is substantially stagnant relative to the plates, wherein the uniform thickness of the layer is confined by the sample contact areas of the two plates and is regulated by the plates and the spacers;
  wherein the first plate and the second plate are configured to confine at least part of the sample into a layer of highly uniform thickness of 0.1-200 um and substantially stagnant relative to the plates;
  wherein the first plate has a thickness of 500 um or less, and the second plate has a thickness of 5 mm or less.

JJ2. The device of any prior embodiments, wherein the plates and the sample thickness are configured to allow a temperature of the sample changed at a rate of 10° C./s or higher.

JJ3. The device of any prior embodiments, further comprising a clamp that compresses the first plate and the second plate to fix the two plates together at the closed configuration, wherein the pressure of the clamp inserted on the plates is 0.01 kg/cm^2 or higher, JJ4. The device of any prior embodiments, wherein the heating layer is on or near of one of the plates, has an absorption coefficient of 60% or higher, and has a thickness of less than 2 mm.

JJ5. The device of any prior embodiments, further comprising a radiation absorbing lay near the at least part of the sample of uniform thickness, whereas the area of the at least part of the sample and radiation absorbing layer are substantially larger than the uniform thickness.

JJ6. The device of any prior embodiments, wherein the area of the at least part of the sample and the radiation absorbing layer are substantially larger than the uniform thickness of the sample.

JJ7. The device of any prior embodiments, wherein the device has one of the plates of a thickness of 100 um or less.

JJ8. The device of any prior embodiments, further comprising a radiation absorbing lay near the at least part of the sample of uniform thickness, wherein the device has one of the plates of a thickness of 100 um or less.

JJ9. The device of any prior embodiments, further comprising a clamp that compresses the first plate and the second plate together in the closed configuration, wherein the pressure of the clamp inserted on the plates is 0.01 kg/cm^2 or higher.

JJ10. The device of any prior embodiments, further comprising a clamp that compresses the first plate and the second plate together in the closed configuration, and further comprising a radiation absorbing lay near the at least part of the sample of uniform thickness, wherein the pressure of the clamp inserted on the plates is 0.01 kg/cm^2 or higher.

JJ11. A system for rapidly changing temperature of a thin fluidic sample layer, comprising:
  v. a device of any prior claims,
  vi. a radiation source, wherein the radiation source is configured to radiate electromagnetic waves that the radiation absorbing layer absorbs significantly; and
  vii. a controller is configured to control the radiation source and change the temperature of the sample.

JJ12. A method for rapidly changing temperature of a thin fluidic sample layer, comprising:
  vi. providing a device or a system of any prior claims;
  vii. depositing a fluid sample on one or both of the plates of the device;
  viii. after ii, pressing the plates into a closed configuration wherein the plates compress at least a part of the sample into a thin layer of a thickness less than 200 um; and
  ix. changing and maintaining the temperature of the sample layer by changing the presence, intensity, wavelength, frequency, and/or angle of the electromagnetic waves from the radiation source.

JJ13. The device, system, or method of any prior embodiments, wherein the clamp is configured to comprise a heat insulator layer to reduce the heat conduction between the clamp and the plates, wherein the heat insulator layer comprises a material of a thermal conductivity of 2 W/m-K.

JJ14. The device, system, or method of any prior embodiments, wherein the clamp is configured to comprise a heat insulator layer to reduce thermal mass that needs to heating or cooling the sample, wherein the heat insulator layer comprises a material of a thermal conductivity of 2 W/m-K.

JJ15. The device, system, or method of any prior embodiments, wherein, in a close configuration, the clamp is configured to seal all the QMAX card.

JJ16. The device, system, or method of any prior embodiments, wherein, in a close configuration, the clamp is configured to have thermal conduction contact with a part of the surface of the plates.

JJ17. The device, system, or method of any prior embodiments, wherein, in a close configuration, the clamp has a thermal conduction contact with only the peripheral surface area of the plates.

JJ18. The device, system, or method of any prior embodiments, wherein, in a close configuration, the clamp has a thermal conduction contact with only a surface area of the plates, wherein the surface area is outside the portion of the sample that nucleic acids to be amplified.

JJ19. The device, system, or method of any prior embodiments, wherein the clamp comprises a window that is transparent allowing light outside going to the plates or the light inside plates going out.

JJ20. The device, system, or method of any prior embodiments, wherein the clamp comprises a window that is transparent allowing light outside going to the plates or the light inside plates going out, wherein the transparence is above 30%, 40%, 50%, 60%, 70%, 80%, 90%, 100%, or a range between any two of the values.

JJ21. The device, system, or method of any prior embodiments, wherein the clamp insert a pressure to compress the first plates and the second plates, wherein the pressure is 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, 400 kg/cm2, or a range between any two of the values.

JJ22. The device, system, or method of any prior embodiments, wherein the clamp insert a pressure to compress the first plates and the second plates, wherein the pressure is from 0.1 kg/cm2 to 20 kg/cm2.

JJ23. The device, system, or method of any prior embodiments, wherein the clamp insert a pressure to compress the first plates and the second plates, wherein the pressure is from 0.1 kg/cm2 to 20 kg/cm2.

JJ24. The device, system, or method of any prior embodiments, wherein the clamp insert a pressure to compress the first plates and the second plates, wherein the pressure is from 0.5 kg/cm2 to 40 kg/cm2.

JJ25. The device, system, or method of any prior embodiments, further comprising a clamp that compresses the first plate and the second plate together in the closed configuration, and further comprising a sealing material between at least part of the first plate and the second plate, wherein the pressure of the clamp inserted on the plates is 0.01 kg/cm^2 or higher.

JJ26. The device, system, or method of any prior embodiments, wherein the changing temperature of the sample is a thermal cycling that changes the temperature up and down in cyclic fashion.

JJ27. The device, system, or method of any prior embodiments, wherein the changing temperature of the sample is a thermal cycling, wherein the thermal cycling is for amplification of nucleic acid using polymerase chain action (PCR).

JJ28. The device, system, or method of any prior embodiments, wherein the changing of the temperature of the sample is for isothermal amplification of nucleic acid.

JJ29. The device, system, or method of any prior embodiments, the area of the at least part of the sample and the radiation absorbing layer are substantially larger than the uniform thickness.

JJ30. The device, system, or method of any prior embodiments, wherein the radiation absorbing layer comprises a disk-coupled dots-on-pillar antenna (D2PA) array, silicon sandwich, graphene, superlattice or other plasmonic materials, other a combination thereof.

JJ31. The device, system, or method of any prior embodiments, wherein the radiation absorbing layer comprises carbon or black nanostructures or a combination thereof.

JJ32. The device, system, or method of any prior embodiments, wherein the radiation absorbing layer is configured to absorb radiation energy.

JJ33. The device, system, or method of any prior embodiments, wherein the radiation absorbing layer is configured to radiate energy in the form of heat after absorbing radiation energy.

JJ34. The device, system, or method of any prior embodiments, wherein the radiation absorbing layer is positioned underneath the sample layer and in direct contact with the sample layer.

JJ35. The device, system, or method of any prior embodiments, wherein the radiation absorbing layer is configured to absorbing electromagnetic waves selected from the group consisting of: radio waves, microwaves, infrared waves, visible light, ultraviolet waves, X-rays, gamma rays, and thermal radiation.

JJ36. The device, system, or method of any prior embodiments, wherein at least one of the plates does not block the radiation that the radiation absorbing layer absorbs.

JJ37. The device, system, or method of any prior embodiments, wherein one or both of the plates have low thermal conductivity.

JJ38. The device, system, or method of any prior embodiments, wherein the uniform thickness of the sample layer is regulated by one or more spacers that are fixed to one or both of the plates.

JJ39. The device, system, or method of any prior embodiments, wherein the sample is a pre-mixed polymerase chain reaction (PCR) medium.

JJ40. The device, system, or method of any prior embodiments, 1, wherein the device is configured to facilitate PCR assays for changing temperature of the sample according to a predetermined program.

JJ41. The device, system, or method of any prior embodiments, wherein the device is configured to conduct diagnostic testing, health monitoring, environmental testing, and/or forensic testing.

JJ42. The device, system, or method of any prior embodiments, wherein the device is configured to conduct DNA amplification, DNA quantification, selective DNA isolation, genetic analysis, tissue typing, oncogene identification, infectious disease testing, genetic fingerprinting, and/or paternity testing.

JJ43. The device of any prior embodiments, wherein the sample layer is laterally sealed to reduce sample evaporation.

JJ44. The system of any of embodiments, further comprising a controller, which is configured to control the presence, intensity, wavelength, frequency, and/or angle of the electromagnetic waves.

JJ45. The system of any prior embodiments, further comprising a thermometer, which is configured to measure the temperature at or in proximity of the sample contact area and send a signal to the controller based on the measured temperature.

JJ46. The system or method of any prior embodiments, wherein the thermometer is selected from the group consisting of: fiber optical thermometer, infrared thermometer, liquid crystal thermometer, pyrometer, quartz thermometer, silicon bandgap temperature sensor, temperature strip, thermistor, and thermocouple.

JJ47. The system or method of any prior embodiments, wherein the controller is configured to control the present, intensity, wavelength, frequency, and/or angle of the electromagnetic waves from the radiation source.

JJ48. The system or method of any prior embodiments, wherein the radiation source and the radiation absorbing layer are configured that the electromagnetic waves cause an average ascending temperature rate ramp of at least 10° C./s;

and the removal of the electromagnetic waves results in an average descending temperature rate ramp of at least 5° C./s.

JJ49. The device, system, or method of any prior embodiments, wherein the radiation source and the radiation absorbing layer are configured to create an average ascending temperature rate ramp of at least 10° C./s and an average descending temperature rate ramp of at least 5° C./s.

JJ50. The device, system, or method of any prior embodiments, wherein the radiation source and the radiation absorbing layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

JJ51. The device, system, or method of any prior embodiments, wherein the PCR sample comprises: template DNA, primer DNA, cations, polymerase, and buffer.

JJ52. The method of any prior embodiments, wherein the step of pressing the plates into a closed figuration comprises pressing the plates with an imprecise pressing force.

JJ53. The method of any prior embodiments, wherein the step of pressing the plates into a closed figuration comprises pressing the plates directly with human hands.

JJ54. The method of any prior embodiments, wherein the layer of highly uniform thickness has a thickness variation of less than 10%.

JJ55. The device, system, or method of any prior embodiments, wherein the changing temperature of the sample is a thermal cycling, wherein the thermal cycling is for amplification of nucleic acid using polymerase chain action (PCR), that is selected from a group of hot-start PCR, nested PCR, touchdown PCR, reverse transcription PCR, RACE PCR, and digital PCR.

JJ56. The device, system, or method of any prior embodiments, wherein the changing of the temperature of the sample is for isothermal amplification of nucleic acid, that is selected from a group of Loop-mediated isothermal amplification, strand displacement amplification, helicase-dependent amplification, nicking enzyme amplification, rolling circle amplification, and recombinase polymerase amplification.

JJ57. The device, system, or method of any prior embodiments, further comprising reagents selected from DNA template, primers, DNA polymerase, deoxynucleoside triphosphates (dNTPs), bivalent cations (e.g. $Mg^{2+}$), monovalent cation (e.g. $K^+$), and buffer solution.

JJ58. The device, system, or method of any prior embodiments, wherein the spacer has substantially flat top.

JJ59. The device, system, or method of any prior embodiments, wherein one of the plates is 50 um or less.

Related Documents

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. Nos. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels

The devices, systems, and methods herein disclosed can employ various types of labels that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents. As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A device for assaying a thin fluidic sample layer, comprising:
   a first plate, a second plate, spacers, and a clamp, wherein:
   i. the first plate and the second plate are movable relative to each other into different configurations, including an open configuration and a closed configuration;
   ii. each of the plates comprises, on its respective surface, a sample contact area for contacting a fluidic sample;
   iii. one or both of the plates comprise the spacers that are fixed to the respective plate;

iv. the spacers have a predetermined substantially uniform height that is equal to or less than 200 microns, wherein at least one of the spacers is inside the sample contact area;

v. a heating layer configured to heat the fluidic sample; and vi. the clamp clamps the outside of the first plate and the second plate to fix the plates in the closed configuration during heating, wherein the heating layer is (a) on or near the inner or outer surface of one of the plates or inside one of the plates, and (b) capable of being heated by a heating source, wherein the heating source delivers heat energy to the heating layer optically, electrically, by radio frequency (RF) radiation, or a combination thereof;

wherein in an open configuration, the two plates are partially or completely separated apart, the spacing between the plates is not regulated by the spacers, and the sample is deposited on one or both of the plates;

wherein in a closed configuration, which is configured after the sample is deposited in the open configuration, at least a part of the sample is compressed by the two plates into a layer of substantially uniform thickness and is substantially stagnant relative to the plates, wherein the uniform thickness of the layer is confined by the sample contact areas of the two plates and is regulated by the plates and the spacers;

wherein the first plate and the second plate are configured to confine at least part of the sample into a layer of highly uniform thickness of 0.1-200 um and substantially stagnant relative to the plates;

wherein the first plate has a thickness of 200 um or less, and the second plate has a thickness of 2 mm or less.

2. The device of claim 1, wherein the plates and the sample thickness are configured to allow a temperature of the sample changed at a rate of 10° C./s or higher.

3. The device of claim 1, wherein the clamp is configured to seal the two plates at the closed configuration, and wherein the pressure of the clamp exerted on the plates is 0.01 kg/cm^2 or higher.

4. The device of claim 1, wherein the heating layer is on or near one of the plates, has an absorption coefficient of 60% or higher, and has a thickness of less than 2 mm.

5. The device of claim 1, further comprising a radiation absorbing layer near the at least part of the sample of uniform thickness.

6. The device of claim 5, wherein the area of the at least part of the sample and the radiation absorbing layer are substantially larger than the uniform thickness of the sample.

7. The device of claim 1, wherein one of the plates has a thickness of 100 um or less.

8. The device of claim 1, further comprising a radiation absorbing layer near the at least part of the sample of uniform thickness, wherein one of the plates has a thickness of 100 um or less.

9. The device of claim 1, wherein the pressure of the clamp exerted on the plates is 0.01 kg/cm^2 or higher.

10. The device of claim 1, further comprising a radiation absorbing layer near the at least part of the sample of uniform thickness, wherein the pressure of the clamp exerted on the plates is 0.01 kg/cm^2 or higher.

11. The device of claim 1, wherein the clamp comprises a heat insulator layer to reduce the heat conduction between the clamp and the plates, wherein the heat insulator layer comprises a material of a thermal conductivity of 2 W/m-K.

12. The device of claim 1, wherein the clamp comprises a heat insulator layer to reduce the thermal mass for heating or cooling the sample, wherein the heat insulator layer comprises a material of a thermal conductivity of 2 W/m-K.

13. The device of claim 1, wherein, in the closed configuration, the clamp is configured to seal all of the first plate and the second plate.

14. The device of claim 1, wherein, in the closed configuration, the clamp is configured to have thermal conduction contact with a part of the surface of the plates.

15. The device of claim 1, wherein, in the closed configuration, the clamp has a thermal conduction contact with only the peripheral surface area of the plates.

16. The device of claim 1, wherein, in the closed configuration, the clamp has a thermal conduction contact with only a surface area of the plates, wherein the surface area is outside the portion of the sample in which nucleic acids are to be amplified.

17. The device of claim 1, wherein the clamp comprises a window that is transparent allowing light from outside of the plates to go to the plates or light from inside of the plates to go out of the plates.

18. The device of claim 1, wherein the clamp comprises a window that is transparent allowing light from outside of the plates to go to the plates or light from inside of the plates to go out of the plates, wherein the transparence is above 30%, 40%, 50%, 60%, 70%, 80%, 90%, 100%, or a range between any two of the values.

19. The device of claim 1, wherein the clamp exerts a pressure to compress the first plates and the second plates, wherein the pressure is 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, 400 kg/cm2, or a range between any two of the values.

20. The device of claim 1, wherein the clamp exerts a pressure to compress the first plate and the second plate, wherein the pressure is from 0.1 kg/cm2 to 20 kg/cm2.

21. The device of claim 1, wherein the clamp exerts a pressure to compress the first plate and the second plate, wherein the pressure is from 0.1 kg/cm2 to 20 kg/cm2.

22. The device of claim 1, wherein the clamp exerts a pressure to compress the first plate and the second plate, wherein the pressure is from 0.5 kg/cm2 to 40 kg/cm2.

23. The device of claim 1, further comprising a sealing material between at least part of the first plate and the second plate, wherein the pressure of the clamp exerted on the plates is 0.01 kg/cm^2 or higher.

24. The device of claim 1, wherein at least one of the plates does not block the radiation that the radiation absorbing layer absorbs.

25. The device of claim 1, wherein one or both of the plates have low thermal conductivity.

26. The device of claim 1, wherein the sample is a pre-mixed polymerase chain reaction (PCR) medium.

27. The device of claim 26, wherein the PCR sample comprises: a template DNA, a primer DNA, cations, a polymerase, and a buffer.

28. The device of claim 1, wherein the device is configured to facilitate PCR assays for changing temperature of the sample according to a predetermined program.

29. The device of claim 1, wherein the device is configured to conduct diagnostic testing, health monitoring, environmental testing, and/or forensic testing.

30. The device of claim 1, wherein the device is configured to conduct DNA amplification, DNA quantification, selective DNA isolation, genetic analysis, tissue typing, oncogene identification, infectious disease testing, genetic fingerprinting, and/or paternity testing.

31. The device of claim 1, wherein the sample layer is laterally sealed by the clamp in the closed configuration to reduce sample evaporation.

32. The device of claim 1, further comprising reagents selected from DNA template, primers, DNA polymerase, deoxynucleoside triphosphates (dNTPs), bivalent cations, monovalent cation, and buffer solution.

33. The device of claim 1, wherein the spacer has a substantially flat top.

34. The device of claim 1, wherein the thickness of one of the plates is 50 um or less.

35. A system for rapidly changing temperature of a thin fluidic sample layer, comprising:
  i. the device of claim 5,
  ii. a radiation source, wherein the radiation source is configured to radiate electromagnetic waves that the radiation absorbing layer absorbs significantly; and
  iii. a controller is configured to control the radiation source and change the temperature of the sample.

36. The device of claim 5, wherein the radiation absorbing layer comprises a disk-coupled dots-on-pillar antenna (D2PA) array, a silicon sandwich, a graphene, a superlattice, a plasmonic material, or a combination thereof.

37. The device of claim 5, wherein the radiation absorbing layer comprises carbon, a black nanostructure or a combination thereof.

38. The device of claim 5, wherein the radiation absorbing layer is configured to absorb radiation energy.

39. The device of claim 5, wherein the radiation absorbing layer is configured to radiate energy in the form of heat after absorbing radiation energy.

40. The device of claim 5, wherein the radiation absorbing layer is positioned underneath the sample layer and is in direct contact with the sample layer.

41. The device of claim 5, wherein the radiation absorbing layer is configured to adsorb electromagnetic waves selected from the group consisting of: radio waves, microwaves, infrared waves, visible light, ultraviolet waves, X-rays, gamma rays, and thermal radiation.

42. The system of claim 35, wherein the changing temperature of the sample is a thermal cycling, wherein the thermal cycling is for amplification of nucleic acid using polymerase chain action (PCR), that is selected from a group of hot-start PCR, nested PCR, touchdown PCR, reverse transcription PCR, RACE PCR, or digital PCR.

43. The system of claim 35, wherein the changing of the temperature of the sample is for isothermal amplification of nucleic acid, that is selected from a group of Loop-mediated isothermal amplification, strand displacement amplification, helicase-dependent amplification, nicking enzyme amplification, rolling circle amplification, or recombinase polymerase amplification.

44. The system of claim 35, wherein the changing temperature of the sample is a thermal cycling that changes the temperature up and down in cyclic fashion.

45. The system of claim 35, wherein the changing temperature of the sample is a thermal cycling, wherein the thermal cycling is for amplification of nucleic acid using polymerase chain action (PCR).

46. The system of claim 35, wherein the changing of the temperature of the sample is for isothermal amplification of nucleic acid.

47. The system of claim 35, further comprising a controller configured to control the presence, intensity, wavelength, frequency, and/or angle of the electromagnetic waves.

48. The system of claim 35, further comprising a thermometer configured to measure the temperature at or in proximity of the sample contact area and send a signal to the controller based on the measured temperature.

49. The system or method of any prior claims of claim 48, wherein the thermometer is selected from the group consisting of: fiber optical thermometer, infrared thermometer, liquid crystal thermometer, pyrometer, quartz thermometer, silicon bandgap temperature sensor, temperature strip, thermistor, and thermocouple.

50. The system of claim 35, wherein the controller is configured to control the presence, intensity, wavelength, frequency, and/or angle of the electromagnetic waves from the radiation source.

51. The system of claim 35, wherein the radiation source and the radiation absorbing layer are configured so that the electromagnetic waves cause an average ascending temperature rate ramp of at least 10° C./s; and the removal of the electromagnetic waves results in an average descending temperature rate ramp of at least 5° C./s.

52. The system of claim 35, wherein the radiation source and the radiation absorbing layer are configured to create an average ascending temperature rate ramp of at least 10° C./s and an average descending temperature rate ramp of at least 5° C./s.

53. The system of claim 35, wherein the radiation source and the radiation absorbing layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

54. A method for rapidly changing temperature of a thin fluidic sample layer, comprising:
  i. providing the system of claim 35;
  ii. depositing a fluid sample on one or both of the plates of the device;
  iii. after ii, pressing the plates into a closed configuration wherein the plates compress at least a part of the sample into a thin layer of a thickness less than 200 um; and
  iv. changing and maintaining the temperature of the sample layer by changing the presence, intensity, wavelength, frequency, and/or angle of the electromagnetic waves from the radiation source.

55. The method of claim 54, wherein the layer of highly uniform thickness has a thickness variation of less than 10%.

56. The method of claim 54, wherein the step of pressing the plates into a closed figuration comprises pressing the plates directly with a human hand.

57. The method of claim 54, wherein the step of pressing the plates into a closed figuration comprises pressing the plates with an imprecise pressing force.

* * * * *